United States Patent
Frinking et al.

(10) Patent No.: US 8,021,303 B2
(45) Date of Patent: Sep. 20, 2011

(54) SYSTEM FOR EXTRACTING MORPHOLOGICAL INFORMATION THROUGH A PERFUSION ASSESSMENT PROCESS

(75) Inventors: Peter Frinking, Genéve (CH); Marcel Arditi, Genéve (CH); Nicolas Rognin, Genéve (CH)

(73) Assignee: Bracco Research SA, Geneve (CH)

( * ) Notice: Subject to any disclaimer, the term of this patent is extended or adjusted under 35 U.S.C. 154(b) by 1121 days.

(21) Appl. No.: 11/823,098

(22) Filed: Jun. 25, 2007

(65) Prior Publication Data

US 2008/0294027 A1    Nov. 27, 2008

Related U.S. Application Data

(63) Continuation-in-part of application No. 11/302,415, filed as application No. PCT/EP2004/051090 on Jun. 11, 2004, and a continuation-in-part of application No. PCT/EP2005/057068, filed on Dec. 21, 2005.

(30) Foreign Application Priority Data

Jun. 12, 2003 (EP) .................................. 03405423
Dec. 17, 2003 (EP) .................................. 03405903
Dec. 23, 2004 (EP) .................................. 04106952

(51) Int. Cl.
*A61B 8/14* (2006.01)
*A61B 8/06* (2006.01)
(52) U.S. Cl. ...................... 600/458; 600/438
(58) Field of Classification Search ................. None
See application file for complete search history.

(56) References Cited

U.S. PATENT DOCUMENTS 5,860,931 A   1/1999 Chandler
6,080,107 A   6/2000 Poland
6,149,597 A   11/2000 Kamiyama
(Continued)

FOREIGN PATENT DOCUMENTS

EP    0458745    11/1991
(Continued)

OTHER PUBLICATIONS

International Search Report for International Patent Application Serial No. PCT/EP2005/057065; European Patent Office, Oct. 25, 2006.

(Continued)

*Primary Examiner* — Long V. Le
*Assistant Examiner* — Angela M Hoffa
(74) *Attorney, Agent, or Firm* — Dylan O. Adams; Graybeal Jackson LLP

(57) ABSTRACT

A perfusion assessment system is proposed. The system includes means for providing an echo-power signal indicative of a reperfusion of a contrast agent in a body-part of a living subject following destruction of a significant portion of the contrast agent in the body-part, means for associating the echo-power signal to a perfusion function with an S-shape based on a plurality of elementary perfusion functions with said S-shape each one for a corresponding value of at least one perfusion parameter, the elementary perfusion functions being weighted according to a probability density distribution of the at least one perfusion parameter, wherein the S-shape includes an initial portion with substantially zero first derivatives, a final portion with substantially zero first derivatives, and a central portion between the initial portion and the final portion changing monotonically from a value of the initial portion to a value of the final portion, means for determining at least one shape indicator of the probability density distribution, and means for comparing the at least one shape indicator with at least one predetermined further shape indicator to identify morphological characteristics of the body-part according to a result of the comparison.

19 Claims, 7 Drawing Sheets

U.S. PATENT DOCUMENTS

| | | | |
|---|---|---|---|
| 6,315,730 | B1* | 11/2001 | Hoff et al. .................. 600/458 |
| 6,461,303 | B2 | 10/2002 | Angelsen |
| 6,547,738 | B2 | 4/2003 | Lysyansky |
| 7,054,454 | B2 | 5/2006 | Causevic et al. |
| 7,415,142 | B2 | 8/2008 | Breeuwer |
| 7,753,850 | B2 | 7/2010 | Averkiou et al. |
| 2002/0029130 | A1 | 3/2002 | Eryurek et al. |
| 2002/0040189 | A1 | 4/2002 | Averkiou et al. |
| 2003/0092991 | A1 | 5/2003 | Sehgal |
| 2003/0114759 | A1 | 6/2003 | Skyba et al. |
| 2003/0185408 | A1 | 10/2003 | Causevic et al. |
| 2006/0161062 | A1* | 7/2006 | Arditi et al. ............... 600/443 |
| 2008/0228080 | A1* | 9/2008 | Arditi et al. ............... 600/458 |

FOREIGN PATENT DOCUMENTS

| | | |
|---|---|---|
| EP | 0554213 | 4/1993 |
| WO | 9115244 | 10/1991 |
| WO | 9409829 | 5/1994 |
| WO | 9516467 | 6/1995 |
| WO | 02056666 | 7/2002 |
| WO | 02102251 | 12/2002 |
| WO | 2004110279 | 12/2004 |
| WO | 2006067201 | 6/2006 |

OTHER PUBLICATIONS

International Search Report for International Patent Application Serial No. PCT/EP2004/051090; European Patent Office, Oct. 1, 2004.

International Search Report for International Patent Application Serial No. PCT/EP2005/057068; European Patent Office, Mar. 20, 2006.

Wei, Kevin, Jayaweera, Ananda R., Firoozan, Soroosh, Linka, Andre, Skyba, Danny M. and Kaul, Sanjiv "Quantification of Myocardial Blood Flow With Ultrasound-Induced Destruction of Microbubbles Administered as a Constant Venous Infusion", Journal of the American Heart Association Circulation 1998; vol. 97; 473-483.

Byrd, Richard H., Schnabel, Robert B., Schultz, Gerald A., "Approximate Solution of the Trust Region Problem by Minimization Over Two-Dimensional Subspaces", University of Colorado at Boulder, Department of Science.

Coleman, Thomas F., Li, Yuying, "An Interior Trust Region Approach for Nonlinear Minimization Subject to Bounds"; Siam J. Optimization, Society for Industrial and Applied Mathematics; vol. 6, No. 2, pp. 418-445, May 1996.

Coleman, Thomas F., Li, Yuying, "On the convergence of Interior-reflective Newton Methods for Nonlinear Minimization Subject to Bounds"; the Mathematical Programming Society, Inc. 1994 p. 189-224.

Wei, Kevin, "Detection and Quantification of Coronary Stenosis Severity with Myocardial Contrast Echocardiography" Progress in Cardiovascular Diseases, vol. 44, No. 2, Sep. 10, 2001; p. 81-100.

Wei, Kevin, Le, Elizabeth, Bin, Jian-Ping, Coggins, Matthew, Thorpe, Jerrel, Kaul, Sanjiv, "Quantification of Renal Blood Flow with Contrast-Enhanced Ultrasound"; Journal of the American College of Cardiology; vol. 37 No. 4 2001; p. 1135-1140.

Kharchakdjian, Raffi, Burns, Peter N., Henkelman, Mark; "Fractal Modeling of Microbubble Destruction-reperfusion in Unresolved Vessels"; 2001 IEEE Ultrasonics Symposium p. 1669-1673.

Rim, Se-Joong, Poi-Leong, Howard, Lindner, Jonathan R., Couture, Daniel, Ellegala, Dilantha, Mason, Holland, Durieux, Marcel, Kassel, Neal F., Kaul, Sanjiv; "Quantification of Cerebral Perfusion with "Real-Time" Contrast-Enhanced Ultrasound"; Journal of the American Heart Association Circulation 2001; 104;p. 2582-2581.

Schlosser, Thomas, Pohl, Christoph, Veltmann, Christian, Lohmaier, Stefan, Goenechea, Jon, Ehlgen, Alexander, Koster, Jorg, Bimmel, Dieter, Kuntz-Hehner, Stefanie, Becher, Harald, Tiemann, Klaus; "Feasibility of the Flash-Replenishment Concept in Renal Tissue: Which Parameters Affect the Assessment of the Contrast Replenishment"; Ultrasound in Med & Biol., vol. 27, No. 7,p. 937-944 2001.

Murthy, Thippeswamy H., Li, Peng, Locvicchio, Elizabeth, Baish, Cheryl, Dairywala, Ismail, Armstrong, William F., Vannan, Mani; "Real-Time Myocardial Blood Flow Imaging in Normal Human Beings with the Use of Myocardial Contrast Echocardiography"; American Society of Echocardiography, 2001, p. 698-705.

Kinsler, Lawrence E., Frey, Austin R., Coppens, Alan B., Sanders, James V.; Fundamentals of Acoustics; John Wiley & Sons Third Edition; p. 172-174.

Gautschi, Walter; Handbook of Mathematical Functions; Dover Publications, Inc. New York; p. 295-297.

Veltmann, Christian, Lohmaier, Stefan, Schlosser, Thomas, Shai, Sonu, Ehlgen, Alexander, Pohl, Christoph, Becher, Harald, Tiemann, Klaus; "On the Design of a Capillary Flow Phantom for the Evaluation of Ultrasound Contrast Agents at Very Low Flow Velocities"; Ultrasound in Med. & Biol., vol. 28, No. 5, p. 625-634 2002.

Scabia, Marco, Biagi, Elena, Masotti, Leonardo; "Hardware and Software Platform for Real-Time Processing and Visualization of Echographic Radiofrequency Signals"; IEEE Transactions on Ultrasonics, Ferroelectrics, and Frequency Control, vol. 49, No. 10, Oct. 2002 p. 1444-1452.

Qian, Hong, Bassingthwaighte, James B.; "A Class of Flow Bifurcation Models with Lognormal Distribution and Fractal Dispersion"; J. theor. Biol. Academic Press (2000) p. 205, 261-268.

Krix, Martin, Plathow, Christian, Kiessling, Fabian, Herth, Felix, Karcher, Andreas, Essig, Marco, Schmitteckert, Harry, Kauczor, Hans-Ulrich, Delorme, Stefan; "Quantification of Perfusion of Liver Tissue and Metastases Using a Multivessel Model for Replenishment Kinetics of Ultrasound Contrast Agents"; Ultrasound in Med. & Biol., vol. 30, No. 10 p. 1355-1363, 2004.

Lucidarme, Olivier, Franchi-Abella, Stephanie, Correas, Jean-Michel, Bridal, S. Lori;.Kurtisovski, Erol, Berger, Genevieve; Blood Flow Quantification with Contrast-enhanced US: "Entrance in the Section" Phenomenon-Phantom and Rabbit Study; Experimental Blood Flow Quantification: "Entrance in the Section" Phenomenon; Radiology; 2003; vol. 228 No. 2, 473-479.

Eyding, Jens, Wilkening, Wilko, Dipl-Ing, Reckhardt, Markus, Schmid, Gebhard, Meves, Saskia, Ermert, Helmut, Przuntek, Horst, Postert, Thomas; "Contrast Burst Depletion Imaging (CODIM) A New Imaging Procedure and Analysis Method for Semiquantitative Ultrasonic Perfusion Imaging"; Stroke, vol. 34, Jan. 2003 p. 77-83; XP002354455.

Cosgrove, David, Eckersly, Robert, Blomley, Martin, Harvey, Christopher; "Quantification of Blood Flow"; Eur. Radiol. (2001) vol. 11, No. 8, 2001, 1338-1344.

* cited by examiner

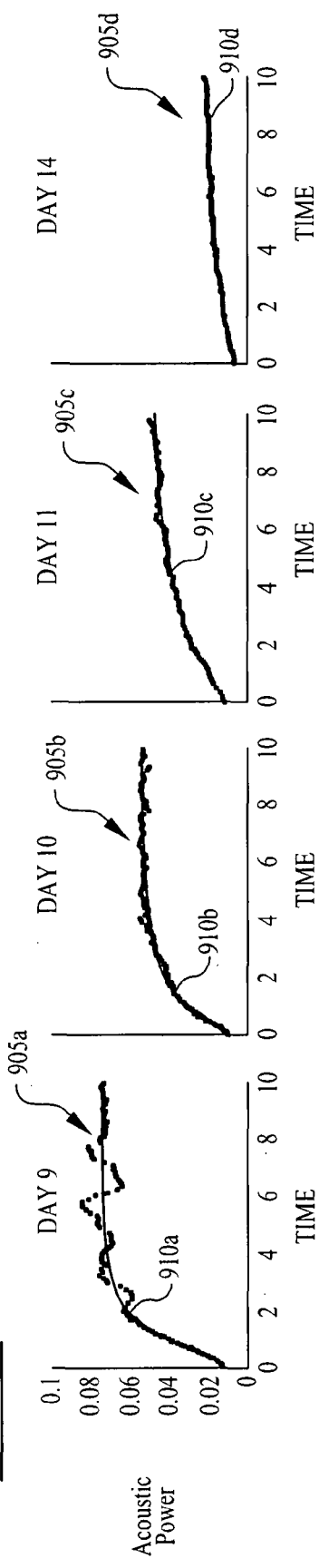
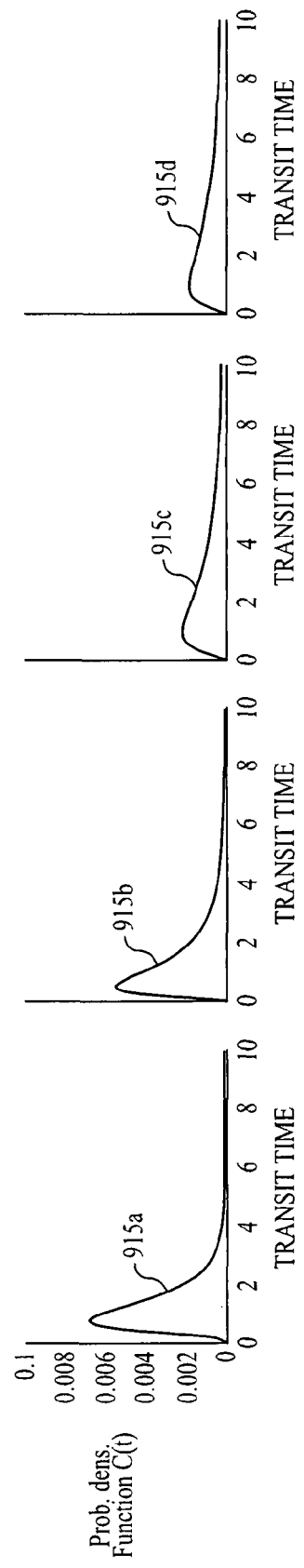
FIG. 9A
FIG. 9B

US 8,021,303 B2

SYSTEM FOR EXTRACTING MORPHOLOGICAL INFORMATION THROUGH A PERFUSION ASSESSMENT PROCESS

PRIORITY CLAIM

This is a continuation-in-part application which claims priority from PCT/EP2005/057068, published in English, filed Dec. 21, 2005, which claims priority from European patent Application No. 04106952.7, filed Dec. 23, 2004. This is also a continuation-in-part of U.S. application Ser. No. 11/302,415, filed Dec. 12, 2005, which claims priority from PCT/EP2004/051090, published in English, filed Jun. 11, 2004, which claims priority from European patent Application No. 03405423.9, filed Jun. 12, 2003 and European patent Application No. 03405903.0, filed Dec. 17, 2003. All of the above applications are incorporated herein by reference.

CROSS REFERENCE TO RELATED APPLICATIONS

This application is related to U.S. patent application Ser. No. 11/794,182, filed Jun. 25, 2007, entitled A PERFUSION ASSESSMENT METHOD AND SYSTEM BASED ON BOLUS ADMINISTRATION, which is incorporated by reference.

TECHNICAL FIELD

An embodiment of the present invention relates to the diagnostic imaging field. More specifically, an embodiment of the present invention relates to blood perfusion assessment through echo-power signal analysis of a contrast agent; particularly, an embodiment of the invention is aimed at facilitating the identification of morphological characteristics of a body-part under analysis.

BACKGROUND

Diagnostic imaging is an emerging technique in the field of medical equipment. For example, this technique is typically exploited for the assessment of blood perfusion, which finds use in several diagnostic applications and especially in ultrasound analysis. The perfusion assessment is based on the analysis of a sequence of ultrasound contrast images, obtainable by administering an ultrasound contrast agent (UCA) to a living subject. The contrast agent acts as an efficient ultrasound reflector, so that it can be easily detected applying ultrasound waves and measuring a resulting echo-signal. As the contrast agent flows at the same velocity as the blood in the subject, its tracking provides information about the perfusion of the blood in a body-part to be analyzed.

Suitable contrast agents include suspensions of gas bubbles in a liquid carrier. For this purpose, the gas bubbles are stabilized using emulsifiers, oils, thickeners or sugars, or by entraining or encapsulating the gas or a precursor thereof into a variety of systems. Stabilized gas bubbles are generally referred to as gas-filled microvesicles. The microvesicles include gas bubbles dispersed in an aqueous medium and bound at the gas/liquid interface by a very thin envelope involving a surfactant, i.e., an amphiphilic material (also known as microbubbles). Alternatively, the microvesicles include suspensions in which the gas bubbles are surrounded by a solid material envelope formed of natural or synthetic polymers (also known as microballoons or microcapsules). Another kind of ultrasound contrast agent includes suspensions of porous microparticles of polymers or other solids, which carry gas bubbles entrapped within the pores of the microparticles. Examples of suitable aqueous suspensions of microvesicles, in particular microbubbles and microballoons, and of the preparation thereof are described in EP-A-0458745, WO-A-91/15244, EP-A-0554213, WO-A-94/09829 and WO-A-95/16467, which are incorporated by reference.

The perfusion assessment process is typically implemented with the so-called destruction-replenishment technique. For this purpose, the body-part to be analyzed is first perfused with the contrast agent at a constant rate. The microbubbles are then destroyed by a flash of sufficient energy. Observation of the replenishment (or reperfusion) of the microbubbles in the body-part provides quantitative information about the local blood perfusion. For this purpose, the intensity of the echo-signal that is measured over time is fitted by a mathematical model, in order to extract quantitative indicators of blood perfusion; the information thus obtained can then be used to infer a physiological condition of the body-part. This technique has been proposed for the first time in Wei, K., Jayaweera, A. R., Firoozan, S., Linka, A., Skyba, D. M., and Kaul, S., "Quantification of Myocardial Blood Flow With Ultrasound-Induced Destruction of Microbubbles Administered as a Constant Venous Infusion," Circulation, vol. 97 1998, which is incorporated by reference.

The above-described process has typically been borrowed from the indicator-dilution theory, which describes the time evolution of a concentration of an indicator as it is randomly diluted in a homogeneous medium. Indeed, prior investigators have been based their approach mostly on the intensity observed during the perfusion process, which is a quantity strongly determined by the so-called log-compression of the equipments that are generally used. This has led to the choice of a mathematical model consisting of a mono-exponential function I(t) (of the video gray level against time) with a general form given by:

$$I(t) = A \cdot (1 - e^{-\beta t})$$

where A is the steady-state amplitude, $\beta$ is a "velocity" term of the mono-exponential function, and the time origin is taken at the instant immediately following the last destruction pulses. In the prior art (e.g., the cited articles by Wei et al.), the values A, $\beta$ and A$\beta$ have commonly been interpreted as quantities proportional to "blood volume", "blood velocity" and "blood flow" within the body-part under analysis.

However, it has been observed that the known approach is very sensitive to the equipments used and to their settings (such as receiver gain, log-compression, and so on). Therefore, the perfusion parameters that are extracted cannot be compared between investigators using different equipments or settings. Furthermore, the perfusion parameters so obtained are only relative estimates, and are often not suitable for an absolute quantitative evaluation.

A further drawback of at least some of the solutions known in the art is that the above-described perfusion parameters (i.e., blood volume, velocity, and flow) can only provide an indication of the integrity of the tissue forming the body-part under analysis. These so-called haemodynamic parameters contain no information about the morphology of the microvascular network of the body-part (i.e., its configuration and structure). Therefore, available solutions may be ineffective in identifying pathologies that cause changes in the morphology of the vascularity of the body-part under analysis, with or without changes of its haemodynamic parameters.

SUMMARY

An embodiment of the present invention proposes a solution, which is based on the idea of estimating the morphology of the body-part under analysis according to the probability density distribution of perfusion parameters.

Particularly, an embodiment of the present invention proposes a perfusion assessment system. The system includes means for providing an echo-power signal indicative of a reperfusion of a contrast agent in a body-part of a living subject (following destruction of a significant portion of the contrast agent in the body-part). Means is provided for associating the echo-power signal to a perfusion function with an S-shape. The perfusion function is based on a plurality of elementary perfusion functions with said S-shape, each one for a corresponding value of one or more perfusion parameters; the elementary perfusion functions are weighted according to a probability density distribution of the perfusion parameter. The S-shape includes an initial portion with substantially zero first derivatives, a final portion with substantially zero first derivatives, and a central portion (between the initial portion and the final portion) changing monotonically from a value of the initial portion to a value of the final portion. The system further includes means for determining one or more shape indicators of the probability density distribution. Means is then provided for comparing the shape indicator(s) with one or more predetermined further shape indicators, in order to identify morphological characteristics of the body-part according to a result of the comparison.

An embodiment of the proposed solution is independent of the equipment used and of their settings. Therefore, the obtained information can be compared between different investigators (even if they use different equipments or settings). Moreover, this information can be suitable for absolute quantitative evaluations.

More specifically, an embodiment of the devised technique provides information about the morphology of the microvascular network of the body-part. Therefore, this technique is very useful in identifying pathologies that cause changes in the morphology of the vascularity of the body-part under analysis (with or without changes of its haemodynamic parameters).

The different embodiments of the invention described in the following may provide additional advantages.

For example, the shape indicator may be determined by the skewness of the probability density distribution.

This value has been found the most significant one for identifying several pathological conditions; moreover, it consists of a pure number that characterizes the shape of the probability density distribution (irrespectively of the actual values being measured).

In an embodiment of the invention, each elementary perfusion function is a cumulative normal distribution function (based on predetermined parameters of the equipment that has been used to acquire the echo-power signal).

Advantageously, the echo-power signal is made proportional to a concentration of the contrast agent in the body-part (e.g., by linearization of log-compressed images).

In this way, it is possible to associate the echo-power signal to the (S-shape) perfusion function directly (e.g., by a curve fitting process).

Typically, the proposed solution is applied to a temporal sequence of samples representative of the echo-power signal in a region of interest.

This allows obtaining morphological information based on a significant portion of the body-part.

In an embodiment of the invention, the probability density distribution (for example, of the transit time) is assumed to be a lognormal function. In this case, the perfusion function (including the integral of the elementary perfusion functions multiplied by the lognormal function) is represented by corresponding fitting parameters; the shape indicators can then be calculated from these fitting parameters.

An embodiment of the proposed technique is relatively simple, but at the same time effective.

Alternatively, the probability density distribution is represented by a vector of probabilities, so that the perfusion function includes the summation of the elementary perfusion functions multiplied by the corresponding probabilities; in this case, the shape indicators can be calculated from the vector of probabilities.

An embodiment of this implementation allows estimating the actual nature of the probability density distribution.

A way to improve an embodiment of the solution is to obtain a first estimate of the vector of probabilities by minimizing the error between the echo-power signal and the perfusion function. A second estimate of the vector of probabilities (including a higher number of elements) is extrapolated from the first estimate. A third estimate of the vector of probabilities is then determined by means of a neural network, which is initialized according to the second estimate.

An embodiment of the proposed solution strongly improves the accuracy of the results in the presence of noise.

As a further enhancement, the neural network includes a synapsis that is based on weights corresponding to the vector of probabilities; the third estimate is made by training the neural network (iteratively adjusting the weights according to the echo-power signal and corresponding evaluations of the elementary perfusion functions for a predefined set of values of the at least one parameter); in any case, the weights are periodically reset.

An embodiment of the devised technique allows maintaining the weights always positive.

In an embodiment of the invention, the shape indicator (of a body-part with suspected pathological conditions) is compared with the one relating to a further body-part of the living subject that is in a healthy condition.

This makes it possible to identify different pathological conditions of the body-part.

In another embodiment of the invention, the shape indicator is compared with the one relating to the same body-part at a preceding time.

In this case, it is instead possible to monitor the evolution of a specific pathological condition.

An embodiment of the present invention also proposes a diagnostic imaging equipment based on the above-described system (and including ultrasound means for acquiring the echo-power signal).

Another embodiment of the present invention proposes a corresponding perfusion assessment method.

A further embodiment of the present invention proposes a computer program for performing the method.

A still further embodiment of the invention proposes a product embodying the program.

BRIEF DESCRIPTION OF THE DRAWINGS

One or more embodiments of the invention itself, however, as well as features and advantages thereof, will be best understood by reference to the following detailed description, given purely by way of a non-restrictive indication, to be read in conjunction with the accompanying drawings.

FIGS. 9a and 9b show the fitting of experimental data for the same body-part at different days, and the corresponding probability density distributions.

DETAILED DESCRIPTION

Figure 1:
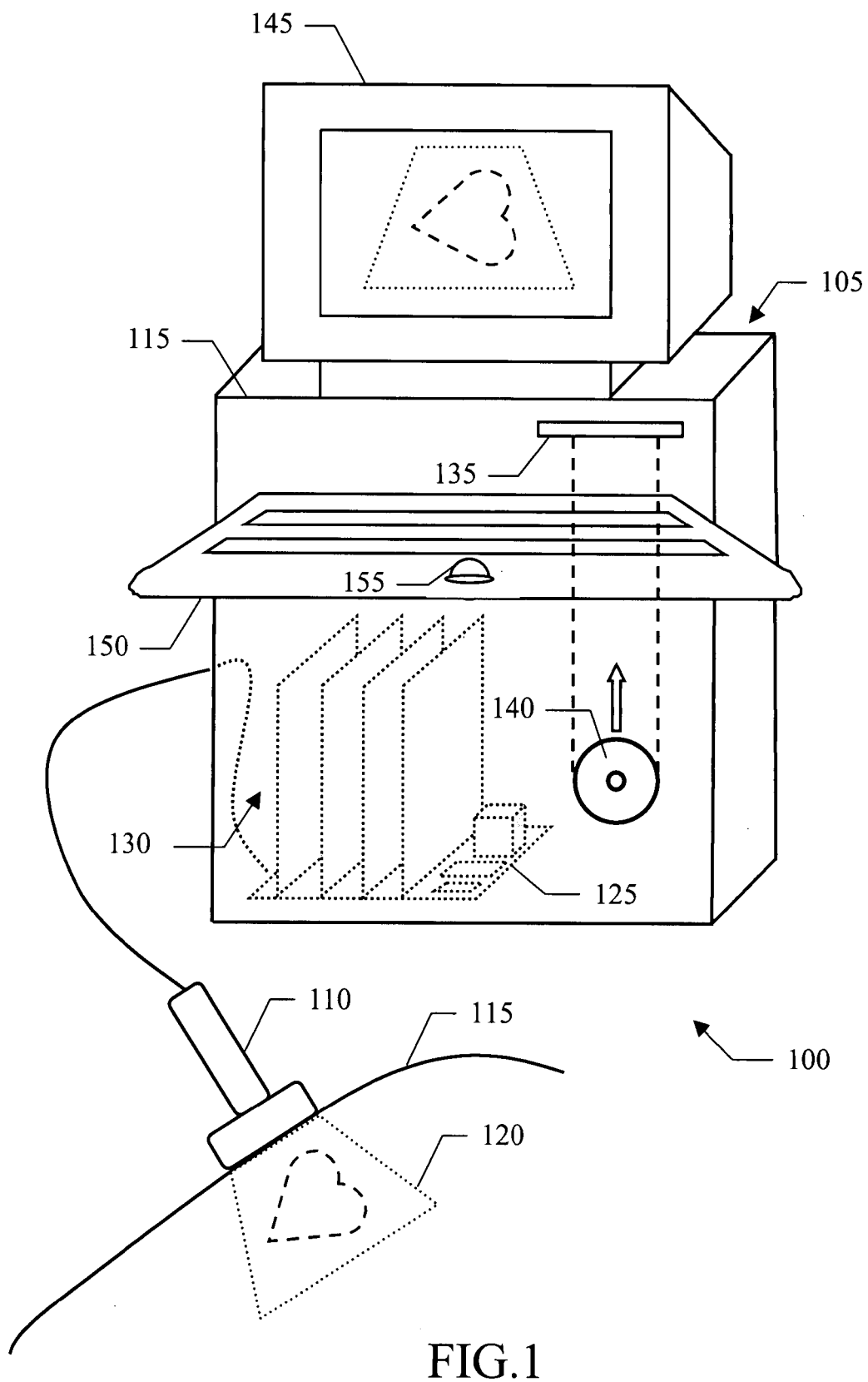
FIG. 1 is a pictorial representation of a diagnostic imaging equipment in which the solution according to an embodiment of the invention is applicable.

With reference in particular to FIG. 1, a diagnostic imaging equipment 100 is illustrated. Particularly, the equipment 100 consists of an ultrasound scanner having a central unit 105 with a hand-held transmit-receive array probe 110 (of the linear or matrix type). The probe 110 transmits ultrasound waves (for example, having a center frequency between 2 and 10 MHz), and receives echo-power signals resulting from the reflection of the ultrasound waves (when in contact with the skin of a patient 115 in the area of a body-part 120 to be analyzed); for this purpose, the probe 110 is provided with a transmit/receive multiplexer, which allows using the probe 110 in the above-mentioned pulse-echo mode.

The central unit 105 houses a motherboard 125, on which the electronic circuits controlling operation of the scanner 100 (such as a microprocessor, a working memory and a hard-disk drive) are mounted. Moreover, one or more daughter boards (denoted as a whole with 130) are plugged on the motherboard 125; the daughter boards 130 provide the electronic circuits for driving the probe 110 and processing its signal. The scanner 100 can also be equipped with a drive 135 for reading removable disks 140 (such as floppy-disks). A monitor 145 is used to display an image representing the body-part 120 under analysis. Moreover, a keyboard 150 is connected to the central unit 105 in a conventional manner; the keyboard 150 is provided with a trackball 155, which is used to manipulate the position of a pointer (not shown in the figure) on a screen of the monitor 145.

The ultrasound scanner 100 is used to assess blood perfusion in the body-part 120. For this purpose, a contrast agent is administered to the patient 115 (typically by injection); the contrast agent is provided with a continuous flow, or as a bolus but in such a way as to reach a fairly constant flow for a sufficient time. After a predetermined period (for example, a few seconds) ensuring that the contrast agent has filled the body-part 120, one of more ultrasound pulses with high acoustic energy (flash) are applied; the acoustic energy must be sufficient (such as with a mechanical index, or MI, of 1-2) to cause the destruction of a significant portion of the microbubbles (for example, at least 50%); this allows the detection of a substantial variation of the received echo-power signal between the value measured right after the application of the destruction pulses and when the body-part is replenished by the contrast agent. A series of ultrasound pulses with low acoustic energy (such as with a mechanical index of 0.01-0.1) is then applied, so as to involve no further destruction of the contrast agent; resulting ultrasound images are recorded continuously (for example, at time intervals of 30-80 ms), in order to track the reperfusion flow of the contrast agent into the body-part 120.

Figure 2:
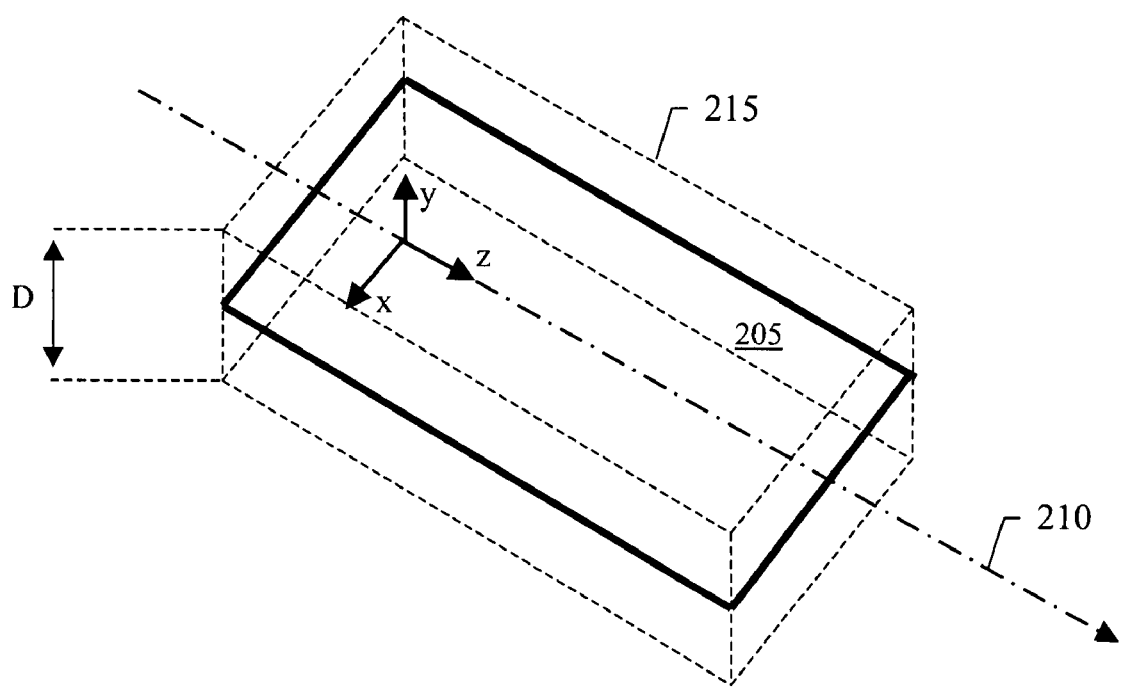
FIG. 2 is a schematic representation of an imaging plane of the equipment.

As shown in FIG. 2, the process is based on a tomographic approach wherein an imaging plane 205 is rapidly scanned by an ultrasound beam propagating along a direction 210. A coordinate system can then be defined with an axis x orthogonal to the propagation direction 210 in the imaging plane 205 (lateral direction), an axis y orthogonal to the imaging plane 205 (elevation direction), and an axis z along the propagation direction 210 (depth direction). The microbubbles are destroyed in a slice 215, which extends symmetrically on either side of the imaging plane 205. The slice 215 has an extension determined by the area scanned by the ultrasound beam, and a thickness D determined by its pressure distribution in the elevation direction y.

The echo-power signal that is measured during the replenishment of the slice 215 by the microbubbles is governed, on the one hand, by the local flow rate of the blood (defining the unknown perfusion parameters to be estimated), and, on the other hand, by the acoustic sensitivity pattern of the probe in essentially the elevation direction y. The acoustic sensitivity pattern can be determined according to the combined effects of its spatial distribution in the transmit mode and in the receive mode (which may be different in general).

Particularly, in the transmit mode an acoustic pressure distribution $p_{Tx}(y)$ in the elevation direction y (assuming a focusing aperture of the probe with rectangular geometry) is approximately given by the function:

$$p_{Tx}(y) \approx \Gamma \cdot \mathrm{sinc}(K_{Tx}y)$$

where $\Gamma$ is an arbitrary proportionality constant and the function sinc(u), for a generic variable u, stands for $$\mathrm{sinc}(u) = \frac{\sin(\pi u)}{\pi u};$$

moreover, $$K_{Tx} = \frac{2a}{\lambda z},$$

with a the prone half-aperture in the elevation direction, $\lambda$ the ultrasound wavelength $$\left(\lambda = \frac{c}{f}\right),$$

with c the speed of sound in the body-part and f the ultrasound frequency), and z the distance from the probe along the depth direction. The above-described function applies to an excitation in the continuous wave mode; in the case of an excitation in the pulsed mode, as is generally the case in the ultrasound scanners, the main lobe of the peak-pressure distribution is in close agreement with the continuous wave case at a frequency near the center (or mean) frequency of the acoustic pulsed waveform.

A corresponding acoustic power distribution P(y) is approximately determined by the square of the pressure distribution p(y), that is:

$$P_{Tx}(y) \approx p_{Tx}^2(y) \approx \mathrm{sinc}^2(K_{Tx}y)$$

In practice, the acoustic power distribution P(y) can be approximated by a normal (or Gaussian) function according to:

$$P_{Tx}(y) \approx e^{-(1.94 \cdot K_{Tx} \cdot y)^2}$$

In the receive mode, a similar approximation of the acoustic power distribution $P_{Rx}(y)$ provides:

$$P_{Rx}(y) \approx e^{-(1.94 \cdot K_{Rx} \cdot y)^2}$$

where the parameter $K_{Rx}$ is determined as indicated above but according to the receive conditions.

An acoustic power sensitivity distribution PE(y) of the probe in the y direction is, in a first approximation, determined by the product of the acoustic power distribution in the transmit mode $P_{Tx}$ (y) and the acoustic power distribution in the receive mode $P_{Rx}$ (y); therefore, the power sensitivity distribution PE(y) can be defined by a normal function as:

$$PE(y) = P_{Tx}(y) \cdot P_{Rx}(y) \approx e^{-(1.94 \cdot K_{Tx} \cdot y)^2} \cdot e^{-(1.94 \cdot K_{Rx} \cdot y)^2} = e^{-(1.94 \cdot y)^2 \cdot (K_{Tx}^2 + K_{Rx}^2)} = e^{-(1.94 \cdot K \cdot y)^2}$$

where the parameter $K^2 = K_{Tx}^2 + K_{Rx}^2$ is determined according to the transmit-receive conditions. This function can also be expressed for values of the unitless quantity $Y = K \cdot y$ as:

$$PE(Y) \approx e^{-(1.94 \cdot Y)^2}.$$

Practically, the value K may be determined theoretically as discussed above; alternatively, the value K may be determined experimentally by scanning a small reflector across the imaging plane 205, in the elevation direction y, and then best fitting the recorded echo-power signal to the above-described function.

Figure 3:
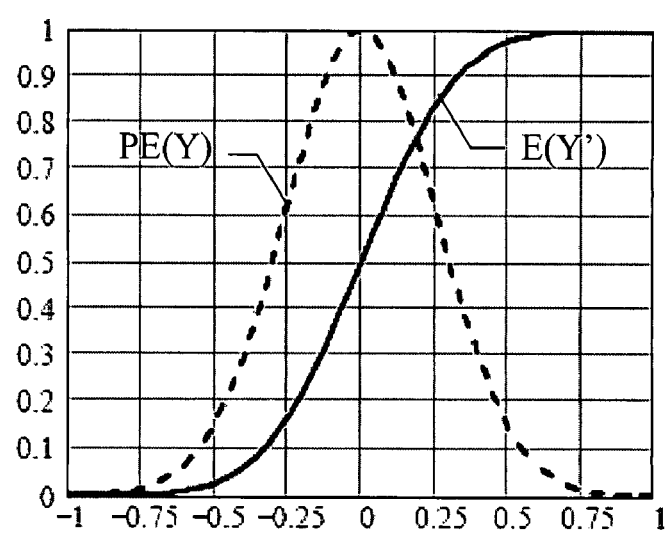
FIG. 3 is a graph showing an exemplary acoustic power distribution of the equipment and its corresponding integral.

As illustrated in FIG. 3, the acoustic power distribution PE(Y) takes its maximum value 1 for Y=0. An acoustic power E(Y') that is measured by the probe when the microbubbles have replenished the slice 215 until a position y'=Y'/K can then be expressed as the integral of the acoustic power sensitivity distribution PE(Y) for the value Y', that is:

$$E(Y') = \int_{-\infty}^{Y'} PE(Y) \, dY$$

As can be seen in the figure, the integral of the acoustic power distribution PE(Y') is represented by a function with an S-shape. The S-shape function includes an initial and a final flat portion (or plateau) with a substantially constant initial value (0 in the example at issue) and final value (1 in the example at issue), respectively; in a central portion between the initial portion and the final portion, the S-shape function changes monotonically from the initial value to the final value (with the half-amplitude value 0.5 that is reached when Y'=0). In other words, the S-shape function has essentially zero first derivatives in its initial and final portions; moreover, the S-shape function may have one or more zero second derivatives in its central portion.

For example, the S-shape function defined by the integral of the acoustic power distribution PE(Y') may be represented by a cumulative normal distribution function (referred to as perf function in this context), as a function of an arbitrary variable q:

$$\text{perf}(q) = \frac{1}{\sqrt{\pi}} \int_{-\infty}^{q} e^{-u^2} \, du$$

Furthermore, the perf function can be simply expressed in terms of an error function erf(q) as:

$$\text{perf}(q) = 0.5 \cdot [1 + \text{erf}(q)]$$

where:

$$\text{erf}(q) = \frac{2}{\sqrt{\pi}} \int_{0}^{q} e^{-u^2} \, du$$

Figure 4:
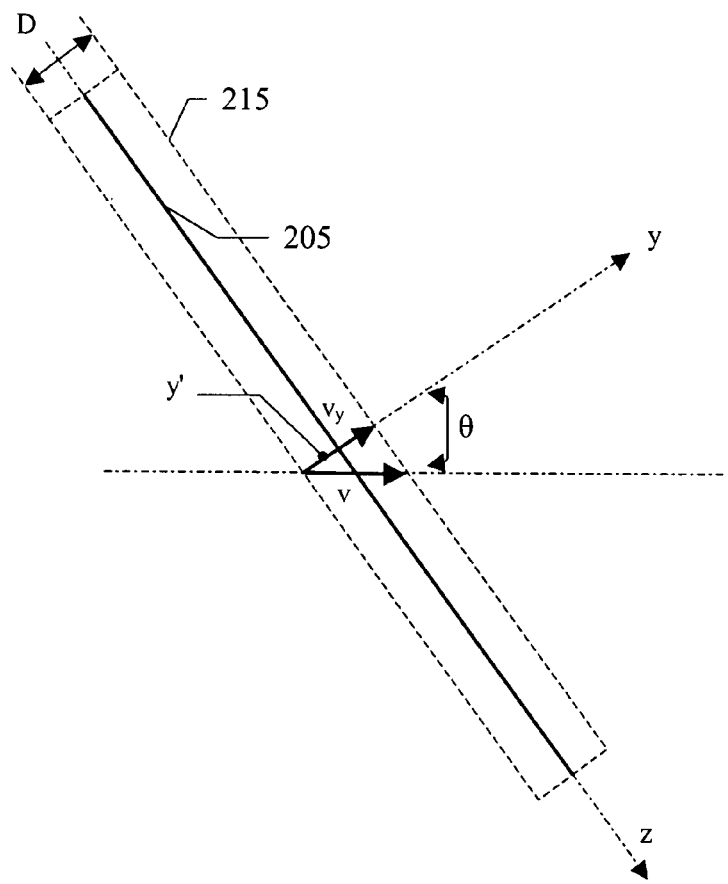
FIG. 4 is a schematic representation of the analysis of a typical perfusion process.

During the reperfusion process, as shown in FIG. 4, the microbubbles replenish the slice 215 with a velocity v; the component of the velocity v along the elevation direction y is then:

$$v_y = v \cdot \cos(\theta)$$

where θ is the angle between the velocity v and the elevation direction y. The location of the microbubbles in the replenishment slice 215 can then be expressed as a function of time as:

$$y' = v_y \cdot (t - \tau)$$

where $$\tau = \frac{D}{2v_y}$$

represents the transit time of the microbubbles in the slice 215, defined as the time delay required for them to travel from the edge of the slice 215 to its central portion (corresponding to the image plane 205). Therefore, the acoustic power that is measured over time during the reperfusion process can be expressed by the following reperfusion function E(t):

$$E(t) = O + A \cdot \text{perf}(q) = O + A \cdot \text{perf}(1.94 \cdot Y')$$
$$= O + A \cdot \text{perf}(1.94 \cdot K \cdot y')$$
$$= O + A \cdot \text{perf}[1.94 \cdot K v_y (t - \tau)]$$

where O and A are an offset parameter and an amplitude parameter, respectively. The perfusion function E(t) may also be expressed in terms of the transit time τ (by replacing $v_y$ with D/2τ):

$$E(t) = O + A \cdot \text{perf}\left[1.94 \cdot \frac{KD}{2\tau}(t - \tau)\right]$$

or in terms of the velocity $v_y$ (by replacing τ with $D/2v_y$):

$$E(t) = O + A \cdot \text{perf}\left[1.94 \cdot \frac{K}{2}(2v_y \cdot t - D)\right].$$

Practically, the value of the thickness D may be tabulated as a function of depth in a reasonable approximation for each ultrasound scanner. Preferably, the thickness D is determined experimentally at different depths. For example, this result can be achieved by embedding microbubbles in a gel and then estimating the extent of destroyed microbubbles by direct optical observation. Alternatively, it is possible to use another ultrasound scanner (at low acoustic power) with its imaging plane perpendicular to the imaging plane of the ultrasound scanner at issue, so as to determine the extent of destroyed microbubbles acoustically (in vivo or in vitro). The thickness D may also be estimated theoretically, on the basis of the transmit beam profile and a knowledge of the threshold in acoustic pressure for microbubbles destruction; a correction factor on the values of the thickness D with depth is then applied by taking into account tissue attenuation.

In actual practice, the microbubbles replenish the slice 215 along multiple directions and with diverse velocities; in this case, the perfusion function E(t) is obtained by combining the different contributions. Particularly, when the microbubbles flow at N velocities $v_{yi}$ (with i=0 ... N) along corresponding directions $\theta_i$ $$\left(\text{and then with transit times } \tau_i = \frac{D}{2v_{yi}}\right)$$

the perfusion function E(t) can be expressed in the continuous form as:

$$E(t) = O + A \cdot \int_0^\infty C(\tau) \cdot \text{perf}\left[1.94 \cdot \frac{KD}{2\tau}(t-\tau)\right] \cdot d\tau$$

or $$E(t) = O + A \cdot \int_0^\infty C(\tau) \cdot \text{perf}\left[1.94 \cdot \frac{K}{2} \cdot (2v_y \cdot t - D)\right] \cdot dv_y,$$

where the function $C(\tau)$ represents a relative concentration of the microbubbles. Likewise, the perfusion function E(t) may also be expressed in the discrete form as:

$$E(t) = O + A \cdot \sum_{i=0}^N C_i \cdot \text{perf}\left[1.94 \cdot \frac{KD}{2\tau_i}(t-\tau_i)\right] \cdot (\tau_{i+1} - \tau_i)$$

or $$E(t) = O + A \cdot \sum_{i=0}^N C_i \cdot \text{perf}\left[1.94 \cdot \frac{K}{2} \cdot (2v_{yi} \cdot t - D)\right] \cdot (v_{yi+1} - v_{yi}),$$

where $C_i$ is the relative concentration of the microbubbles having the transit time or the velocity $v_{yi}$. The relative concentration function $C(\tau)$ and the vector of the relative concentrations $C=[C_0, \ldots, C_N]$ represent the probability density distribution of the corresponding transit times or velocities $$\left(\text{with } 0 \le C(\tau) \le 1 \text{ and } \int_0^\infty C(\tau) d\tau = 1, \text{ or}\right.$$

$$\left. 0 \le Ci \le 1 \text{ and } \sum_{i=0}^N Ci \cdot (\tau_{i+1} - \tau_i) = 1\right).$$

Figure 5:
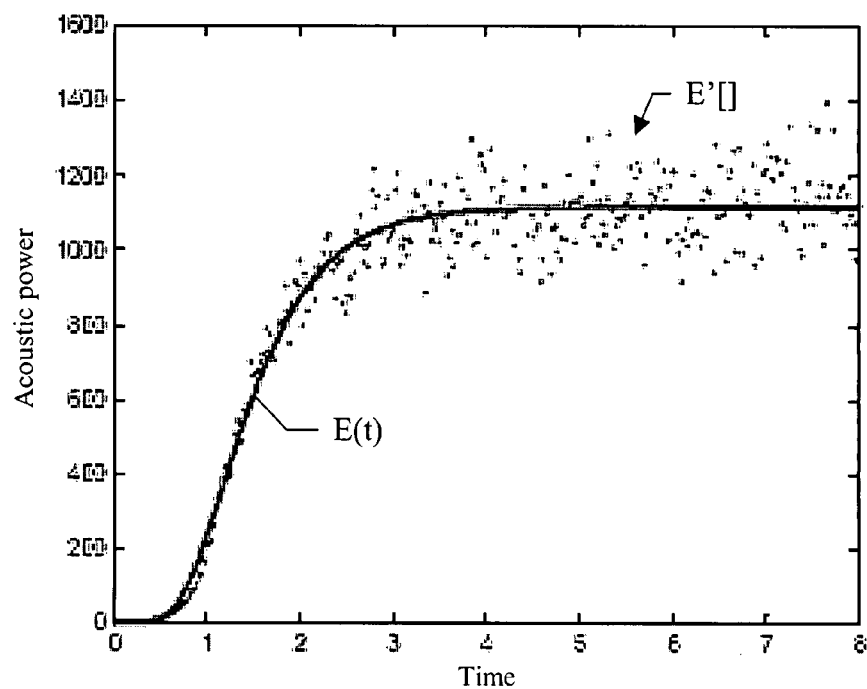
FIG. 5 shows the fitting of experimental data by an S-shape function according to an embodiment of the invention.

With reference now to FIG. 5, the perfusion function E(t) is still graphically represented by an S-shape function. Whenever haemodynamic parameters of the body-part under analysis must be estimated, it has been found beneficial to represent the perfusion function E(t) in the form of a cumulative log-normal function (referred to as logperf function in this context); with reference in particular to the transit time $\tau$, the perfusion function E(t) will be:

$$E(t) = 0 + \frac{A}{2} \cdot \left[1 + \text{erf}\left(\frac{\ln(t) - m}{s\sqrt{2}}\right)\right]$$

where m and s are the mean value and the standard deviation of the natural logarithms of the transit time $\tau$, respectively. The values of the parameters O, A, m and s are estimated by means of a sequence of samples of the acoustic power measured over time; particularly, a vector of samples E'= [E'($t_0$), ... E'($t_M$)] at different times $t_j$ (with j=0 ... M) is fitted by the perfusion function E(t). This result may be achieved using the Trust region method described in Byrd, R. H., R. B. Schnabel, and G. A. Shultz, "Approximate Solution of the Trust Region Problem by Minimization over Two-Dimensional Subspaces", Mathematical Programming, Vol. 40, pp 247-263, 1988 (for example, implemented by the Curve fitting Toolbox of the Matlab® programming language), which is incorporated by reference.

The value of the fitting parameter A provides a good relative estimate of the blood volume in the slice, and the values of the fitting parameters m and s allow determining a good estimate of the mean transit time of the microbubbles ($\tau_{mean}$); in this way, it is also possible to calculate a mean flow rate of the microbubbles as $\phi_{mean} = A/\tau_{mean}$. Similar considerations apply when the mean velocity ($v_{ymean}$) is estimated.

The (haemodynamic) fitting parameters estimated from the analysis of the logperf function exhibit a high linearity with respect to their actual values. Moreover, in sharp contrast to the prior art (i.e., the mono-exponential function), the fitting parameters so obtained are independent of the ultrasound scanner that has been used; in addition, the fitting parameters can now be related to physical quantities.

Besides, it is also possible to obtain information about the morphology of the vascularity of the body-part under analysis by estimating the probability density distribution of the transit times $\tau$. This information is provided by the probability density function $C(\tau)$ (when the perfusion function E(t) is in the continuous form) or by its corresponding discrete probability vector C[ ] (when the perfusion function E(t) is in the discrete form).

For this purpose, in a first embodiment of the invention the probability density function $C(\tau)$ is assumed to have a log-normal distribution, which is the commonly accepted model (i.e., a normal probability density function wherein the natural logarithm is applied to the relevant variable):

$$C(t) = \frac{e^{-\frac{[\ln(\tau) - m]^2}{2s^2}}}{\tau \cdot s\sqrt{2\pi}}$$

where m and s are the mean and standard deviation of the distribution of the natural logarithms of $\tau$, respectively. The sample vector E'[ ] is then fitted by the resulting perfusion function E(t):

$$E(t) = O + A \cdot \int_0^\infty \frac{e^{-\frac{[\ln(\tau) - m]^2}{2s^2}}}{\tau \cdot s\sqrt{2\pi}} \cdot \text{perf}\left[1.94 \cdot \frac{KD}{2\tau}(t-\tau)\right] \cdot d\tau$$

so as to estimate the fitting parameters O, A, m, s. Also in this case, the value of the amplitude parameter A can be related to the relative regional blood volume in the body-part under analysis. However, it is now possible to calculate any desired statistics indicator of the probability density function $C(\tau)$, such as its mean value, variance and skewness:

$$\tau_{mean} = e^{m+\frac{s^2}{2}}$$

$$\sigma^2 = e^{s^2+2m} \cdot (e^{s^2} - 1)$$

$$\gamma = \sqrt{e^{s^2} - 1} \cdot (2 + e^{s^2})$$

Some indicators provide information about the shape of the probability density function $C(\tau)$. For example, the variance $\sigma^2$ measures the spread of the probability density function $C(\tau)$, whereas the skewness $\gamma$ measures its asymmetry. Particularly, the most significant shape indicator is the skewness $\gamma$, since it consists of a pure number independent of the actual values being measured.

Figure 6A:
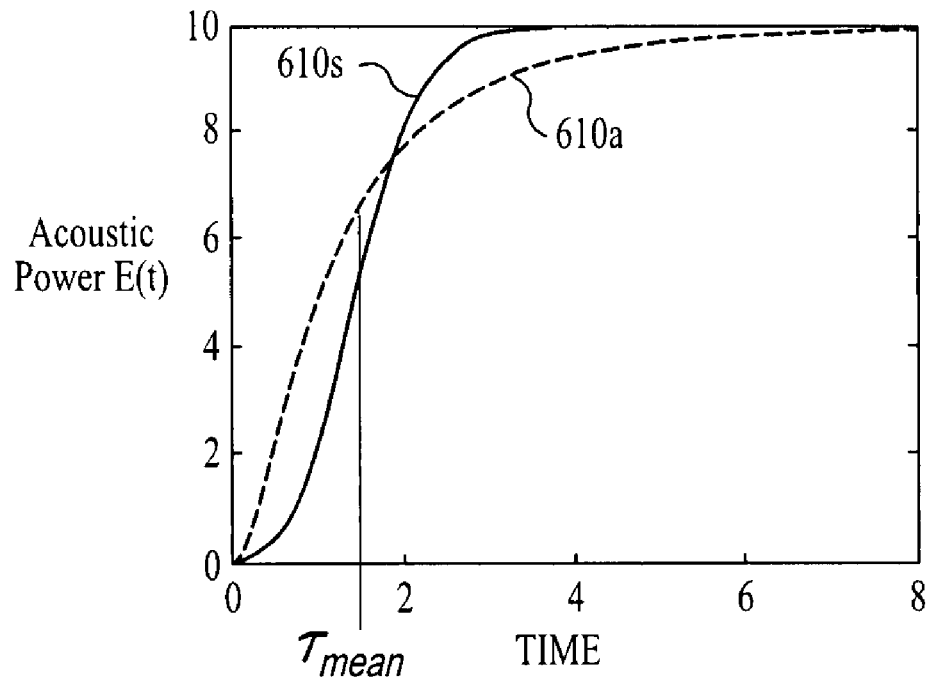
FIGS. 6a and 6b show different examples of perfusion functions with corresponding probability density distributions.

The shape indicators so obtained can be used to characterize the morphology of the vascularity of the body-part under analysis (irrespectively of its haemodynamic parameters). For example, as shown in FIG. 6a, two different perfusion functions E(t) (in terms of an arbitrary unit, or a.u.) are denoted with 610s and 610a. Even though both perfusion functions 610s and 610a have the same mean transit time ($\tau_{mean}=1.48$) and the same value of the amplitude parameter A they are very different in shape. Particularly, the perfusion function 610s is close to the perf function, with a high level of symmetry around its half-amplitude value (5 in the example at issue); conversely, the perfusion function 610a has a distorted shape (with an initial sharper rise and a final softer shoulder), which is clearly asymmetric around the half-amplitude value.

Figure 6B:
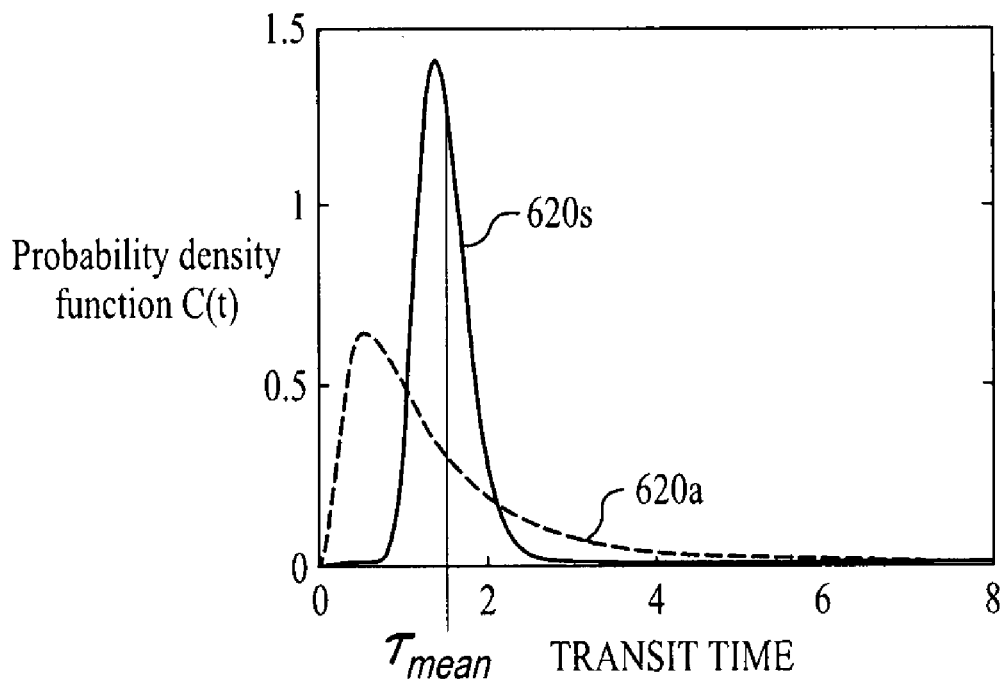

Moving to FIG. 6b, the above-described (symmetric and asymmetric) perfusion functions are instead associated with quite different probability density functions $C(\tau)$. Particularly, the symmetric perfusion function provides a probability density function 620s that is very close to a normal probability density function, being narrow and almost symmetric; this shape is characterized by low values of its variance and skewness ($\sigma^2=0.09$ and $\gamma=0.61$ in the example at issue). Conversely, the asymmetric perfusion function corresponds to a probability density function 620a that is wide and asymmetric; this shape is characterized by high values of its variance and skewness ($\sigma^2=1.97$ and $\gamma=3.69$ in the example at issue).

In this way, it is possible to identify pathological conditions of the body-part under analysis. For example, a nearly symmetric probability density function $C(\tau)$ (with a low skewness $\gamma$) could be associated to healthy tissues (with a very ordered microvascular network); conversely, an asymmetric probability density function $C(\tau)$ (with a high skewness $\gamma$) could be associated to pathological tissues (with a disordered microvascular network). For example, the high skewness $\gamma$ can be indicative of an angiogenic process (i.e., a vascularization of the tissue involving the development of new blood vessels) in cancer, or ischemia in coronary artery disease.

Moreover, it is also possible to monitor the evolution of a pathological condition or the response to a treatment by successive measurements of the shape indicators (and especially the skewness $\gamma$) over time. Indeed, any changes in the skewness $\gamma$ denote a corresponding evolution in the morphology of the vascularity of the body-part. For example, a decrease or an increase of the skewness $\gamma$ can be indicative of the effectiveness of an anti-angiogenic or a pro-angiogenic drug treatment, respectively.

In a different embodiment of the invention, the probability density distribution is estimated without making any assumption about its nature. For this purpose, it may be necessary to fit the sample vector $E'=[\ ]$ by a corresponding perfusion vector $E=[E(t_0), \ldots E(t_M)]$, given by the evaluation of the perfusion function E(t) at the same times $t_j$ (for a vector of predefined transit times $\tau=[\tau_o, \ldots \tau_N]$); preferably, the transit time vector $\tau[\ ]$ is defined by selecting N values in a given interval of interest, according to an arithmetic or geometric progression.

In order to perform the above-described operation, we define a scaled probability vector $C_A=[C_{A0}, \ldots, C_{AN}]=A \cdot [C_0, \ldots, C_N]$, with $C_{Ai}=A \cdot C_i \geq 0$ and $$\sum_{i=0}^{N} C_{Ai} \cdot (\tau_{i+1} - \tau_i) = \sum_{i=0}^{N} A \cdot C_i \cdot (\tau_{i+1} - \tau_i) = A,$$

and a vector of factors $P=[p_0, \ldots, p_N]$, with $p_i=C_{Ai} \cdot (\tau_{i+1}-\tau_i)$. The perfusion vector $E[\ ]$ (assuming the offset parameter O equal to zero for the sake of simplicity) is then a function of the factor vector $P[\ ]$ only. Therefore, we can define an error function between the perfusion vector $E[\ ]$ and the sample vector $E'[\ ]$ in terms of the factor vector $P[\ ]$; for example:

$$err(P) = \sum_{j=0}^{M} |E(P, t_j) - E'(t_j)|$$

The factor vector $P[\ ]$ can be estimated by minimizing the error function err(P), with the constrain that $p_i \geq 0$. Each element of the scaled probability vector $C_A[\ ]$ is then calculated as:

$C_{Ai}=p_i/(\tau_{i+1}-\tau_i)$

It is now possible to estimate the amplitude parameter A by applying the above-mentioned formula $$A = \sum_{i=0}^{N} C_{Ai} \cdot (\tau_{i+1} - \tau_i),$$

and then obtain the probability vector $C[\ ]=C_A[\ ]/A$.

This result may be achieved using the interior-reflective Newton method described in Coleman, T. F. and Y. Li, "An Interior, Trust Region Approach for Nonlinear Minimization Subject to Bounds", SIAM Journal on Optimization, Vol. 6, pp. 418-445, 1996 and in Coleman, T. F. and Y. Li, "On the Convergence of Reflective Newton Methods for Large-Scale Nonlinear Minimization Subject to Bounds", Mathematical Programming, Vol. 67, Number 2, pp. 189-224, 1994 (for example, implemented by the Optimization Toolbox of the Matlab® programming language), which are incorporated by reference. This technique may require the setting of an initial estimate of the factor vector $P[\ ]$. The choice of the initial estimate of the factor vector $P[\ ]$ may be important, since the error function err(P) may have several local minima that allow finding a good approximation of the perfusion function E(t), but not of the factor vector $P[\ ]$. In this case, excellent results were obtained by setting each element of the factor vector $P[\ ]$ as follows:

$p_i=1/N$ or $p_i=(\tau_{i+1}-\tau_i) \cdot [\max(\tau_0, \ldots, \tau_N)]$

It is now possible to calculate any desired statistics indicator of the probability vector C[ ], such as its mean value, variance and skewness:

$$\tau_{mean} = \frac{\sum_{i=0}^{N} C_i \cdot \tau_i}{N}$$

$$\sigma^2 = \frac{\sum_{i=0}^{N} C_i \cdot (\tau_i - \tau_{mean})^2}{N}$$

$$\gamma = \frac{\sum_{i=0}^{N} C_i \cdot \left(\frac{\tau_i - \tau_{mean}}{\sigma}\right)^3}{N}$$

Also in this case, the shape indicators so obtained can be used to characterize the morphology of the vascularity of the body-part under analysis. In addition, it is also possible to detect morphological anomalies in the vascularity of the body-part by comparing the estimated probability density distribution with the lognormal function (characterizing healthy tissues).

Experimental tests have shown that the proposed solution provides good results for echo-power signals with low noise; however, when a non-negligible noise is superimposed to the echo-power signal, the accuracy of the results is impaired.

In this case, it has been found advantageous to apply further estimation steps. For example, in an embodiment of the invention a first estimate of the factor vector P[ ] and then of the scaled probability vector $C_A$[ ] is obtained as described above for a relatively low first number of transit times N; for example, the first number of transit times N is from 4 to 16, and preferably from 6 to 10 (such as 8). A second estimate of the scaled probability vector $C_A$[ ] for a higher second number of transit times N is then extrapolated from the first estimate; the second number of transit times N may be from 8 to 64, for example, from 16 to 48 (such as 32). For example, this result may be achieved by applying a cubic spline interpolation to the first estimate of the scaled probability vector $C_A$[ ]. In detail, the first estimate of the scaled probability vector $C_A$[ ] may be fitted by a cubic smoothing spline function in the transit time domain (for example, using the csaps function of the Matlab® programming language). The cubic smoothing spline function may be evaluated at the second number of transit times N (for example, again uniformly distributed in the interval of interest). A second estimate of each element of the factor vector P[ ] may then be obtained as $p_i = C_{Ai}*(\tau_{i+1} - \tau_i)$.

The second estimate of the factor vector P[ ] is used to initialize a neural network, which performs a third estimation step. As it is well known in the art, a neural network is a data processing system that approximates the operation of the human brain. A neural network consists of basic processing elements (called neurons), which are connected by means of unidirectional channels (called synapses); the neurons (and the corresponding synapses) are organized into one or more layers between an input and an output of the neural network (receiving an input vector IN[ ] and providing an output vector OUT[ ], respectively). The synapse associated with each k-th neuron receives a corresponding input vector $IN_k$[ ] (from other neurons or from the input of the neural network); the synapse multiplies the input vector $IN_k$[ ] by a corresponding weight vector $W_k$[ ] and then adds a bias value $b_k$. The resulting vector $W_k$[ ]·$IN_k$[ ]+$b_k$ in supplied to the associated neuron, which outputs a scalar value $Out_k$[ ] according to a predefined transfer function (for example, the sigmoid or identity function):

$$Out_k[\,] = g(W_k[\,] \cdot IN_k[\,] + b_k)$$

The neural network is initially trained, by providing a large amount of examples (each one consisting of an input vector IN[ ] with the corresponding output vector OUT[ ]); the weight vectors $W_k$[ ] and the bias values $b_k$ are iteratively adjusted so as to fit the available examples. For instance, the training process is performed by minimizing a performance function consisting of the mean square error (mse) between the output vectors OUT[ ] and the input vectors IN[ ].

In this context, a simple neural network with a single synapsis/neuron (implementing a transfer function equal to the identity function) is used; this element (having a weight vector W[ ] of N elements and a bias values b) receives the input vector IN[ ] and provides the output vector OUT[ ] directly (both of them including M elements). Therefore, the performance function mse( ) to be minimized becomes:

$$mse = \frac{1}{M} \|W[\,] \cdot IN[\,] + b - OUT[\,]\|^2$$

If the output vector OUT[ ] is set to the sample vector E'=[ ], the weight vector W[ ] is set to the factor vector P[ ], and the input vector IN[ ] is set to a perf vector Perf[ ] given by the evaluation of the perf function at the times $t_j$ (for the transit time vector τ[ ]), we have the following performance function mse( ) to be minimized:

$$mse = \frac{1}{M} \sum_{j=0}^{M} [P[\,] \cdot perf(t_j) + b - E'(t_j)]^2 = \frac{1}{M} \sum_{j=0}^{M} [E(t_j) + b - E'(t_j)]^2$$

Therefore, the weight vector W[ ] obtained by training the above-described neural network with the perf vector Perf[ ] and the sample vector E'[ ] (assuming that the bias value b is kept as close as possible to zero) provides the desired estimation of the factor vector P[ ] (and then of the probability vector C[ ] as well). For this purpose, the weight vector W[ ] is initialized to the above-mentioned second estimate of the factor vector P[ ]. Moreover, in order to satisfy the constraints that the elements of the weight vector W[ ] are positive and that the bias value b are substantially null, they are periodically reset to zero. The period of the reset operation (in terms of number of iterations) is enough high so as to have the performance function mse( ) decrease significantly (during the training process) before its sharp increase caused by the reset operation; empirically observations provided good results with a period higher then 10, better with a period higher than 25, and even better with a period higher than 50 (for example, up to 200), such 100.

The training process ends when the performance function mse( ) falls below a predefined threshold value. In this respect, acceptable results were obtained with a threshold value between 0.01 and 0.001; particularly, in order to maintain a high accuracy of the training process the threshold value may be reduced as the complexity of the probability density distribution increases or as the period of the reset operation decreases. Advantageously, the stopping condition may not be verified at each iteration of the training process, but only before any reset operation; therefore, the total number of iterations of the training process typically will always be a multiple of the period of the reset operation.

For example, this result can be achieved by using the Matlab® programming language. Particularly, the neural network is created with the newlin function; the performance function (defined by the function net.performFcn) is then minimized with the function traingdx. This function implements a gradient descent algorithm in the batch mode (wherein at each iteration the weights and the bias value are updated only after the entire examples have been applied to the neural network); the function also applies a momentum technique (acting as a low-pass filter that allows ignoring local changes) and an adaptive learning technique (which updates a rate of the gradient descent algorithm dynamically).

Figure 7:
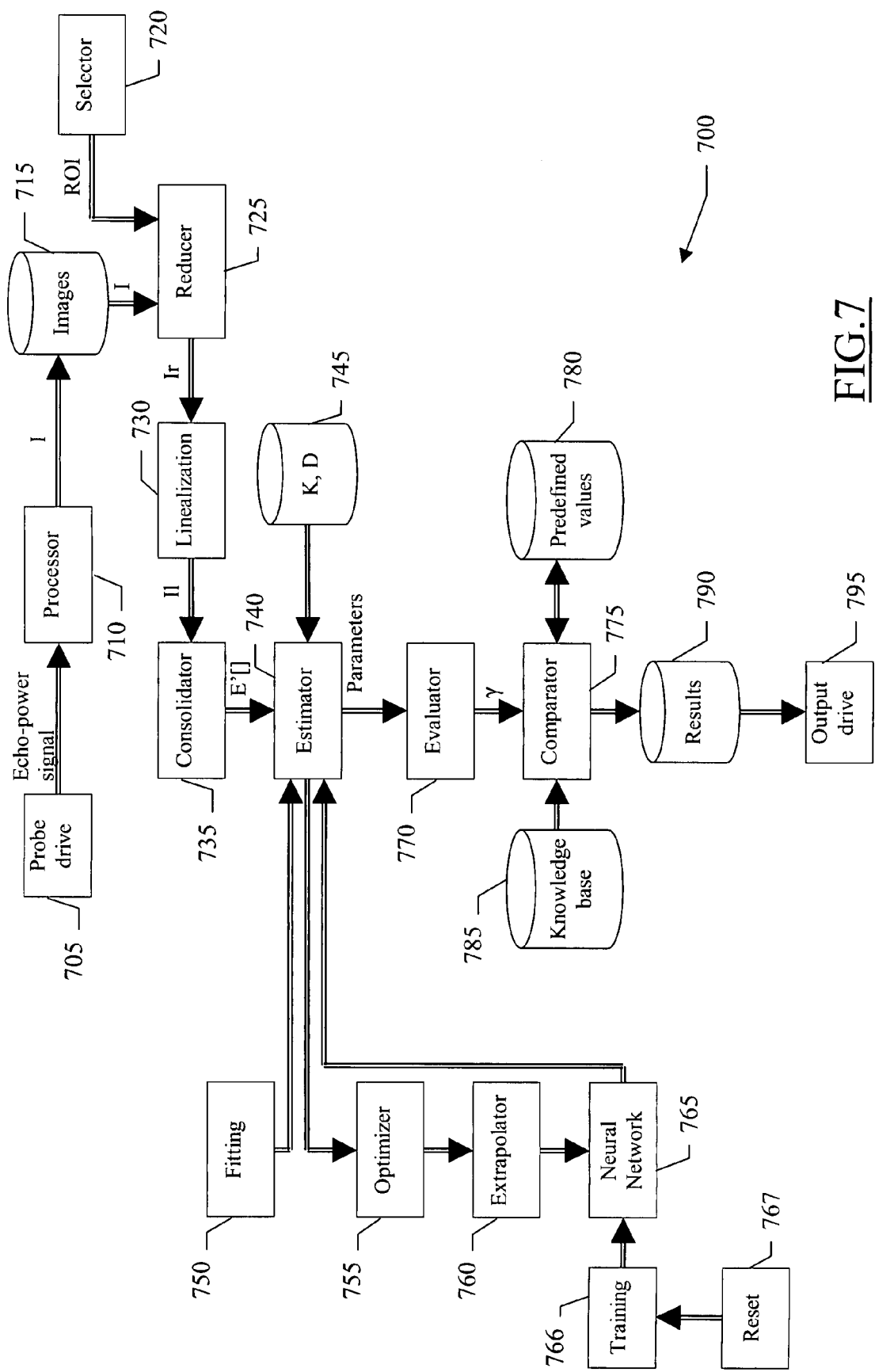
FIG. 7 depicts the main software components that can be used for practicing a perfusion assessment method according to an embodiment of the invention.

Moving now to FIG. 7, the main software components that can be used for practicing a perfusion assessment method according to an embodiment of the invention are denoted as a whole with the reference 700. The information (programs and data) is typically stored on the hard disk and loaded (at least partially) into the working memory when the programs are running, together with an operating system and other application programs (not shown in the figure). The programs are initially installed onto the hard disk, for example, from CD-ROM.

Particularly, a module 705 is used to drive the probe, so as to measure the echo-power signal that is reflected by the body-part being scanned during the perfusion process of the contrast agent; for example, the probe drive 705 includes beam formers and pulsers for generating the ultrasound waves. The measured echo-power signal is supplied to a processor 710. The processor 710 pre-amplifies the echo-power signal and applies a preliminary time-gain compensation (TGC). Typically, the (analog) echo-power signal is then converted into digital values by an Analog-to-Digital Converter (ADC), and combined into a focused signal through a receive beam former. The echo-power signal is also manipulated through digital filters (for example, band-pass filters) and other signal conditioners (for example, post-beam-forming TGC); moreover, the echo-power signal is further manipulated through a demodulator (to extract the amplitude of an echo-envelope) and non-linear conditioners, such as a log compressor (to account for the geometry of the probe). The echo-power signal is optionally compressed again, and then converted into a video format. This process results in a sequence of consecutive images I of the body-part during the perfusion process of the contrast agent, which images I are stored into a corresponding repository 715. Each image consists of a digital representation of the body-part; the image is defined by a matrix (for example, with 512 rows and 512 columns) of visualizing elements, each one representing the intensity of the echo-power signal relating to a basic picture element (pixel) or volume element (voxel).

A selector 720 is used to delimit a region of interest (ROI) for the perfusion assessment on the images; typically, the ROI identifies a significant portion of the body-part to be analyzed. A mask corresponding to the ROI is applied to the sequence of images I by a reducer 725, so as to obtain a corresponding sequence of reduced images Ir with the information relevant to the perfusion process only. A linearization module 730 processes the sequence of reduced images Ir to make each visualizing element proportional to a local concentration of the contrast agent in the corresponding pixel or voxel; for example, this outcome can be achieved by applying an inverse log-compression and then squaring the values of the visualizing elements so obtained. The resulting sequence of linearized images Il is supplied to a consolidator 735. For each linearized image, the consolidator 735 combines the corresponding visualizing elements into a single value indicative of the acoustic power of the whole ROI at the relevant time; for example, this value is calculated as the average of the visualizing elements. This operation provides the sample vector E'[ ]; preferably, the consolidator 735 also applies a median filter to the sample vector E'[ ] (for example, implemented by the function medfild of the Matlab® programming language), so as to reduce the negative effect of any noise.

This sample vector E'[ ] is then supplied to an estimator 740. The module 740 estimates all the fitting parameters of the perfusion function (in the form of the continuous or discrete combination of pert functions weighted by the corresponding probability density function $C(\tau)$ or vector of probabilities C[ ], respectively). For this purpose, the estimator 740 accesses a table 745 storing the values K and D, the a priori knowledge of which is required. The estimator 740 is associated with one or more plug-in modules for implementing the different algorithms described above. For example, a fitting module 750 is used to calculate the probability density function $C(\tau)$ when it is assumed to have a lognormal distribution. In addition or in alternative, an optimizer 755 is used to perform the first estimation of the probability vector C[ ]. The first estimate of the probability vector C[ ] is supplied to an extrapolator 760, which determines its second estimate. The second estimate of the probability vector C[ ] is in turn passed to a neural network module 765. The neural network module 765 is associated with a corresponding training module 766. A reset module 767 is used to force to zero the weights and the bias value of the neural network periodically. The third estimate of the probability vector C[ ] provided by the neural network module 765 is then returned to the estimator 740.

The fitting parameters so obtained are passed to an evaluator 770, which determines the shape indicators for the probability density function $C(\tau)$ or the vector of probabilities C[ ] (for example, its skewness $\gamma$). A module 775 compares the skewness $\gamma$ for the current echo-power signal with one or more predefined values logged in a corresponding repository 780; for example, the repository 780 can store the skewness $\gamma$ obtained for the echo-power signal relating to an alleged healthy body-part, or the skewness $\gamma$ obtained for echo-power signals that were measured previously for the same body-part. Optionally, the comparator 775 also accesses a knowledge base 785, which stores predefined criteria for evaluating the results of the comparison; for example, for each tissue the knowledge base 785 can provide a threshold value of the skewness $\gamma$ (indicative of a healthy condition when not exceeded), can associate different ranges of the skewness $\gamma$ with corresponding pathological conditions, or can establish satisfactory trends of the skewness $\gamma$ over time for different treatments. The results obtained by the comparator 775 are stored into a file 790; for each perfusion assessment, the result file 790 typically lists the compared values, the result of the comparison and possibly a suggested interpretation of the result (according to the information extracted from the knowledge base 785). The information stored in the file 790 is provided to an operator through an output drive 795 (for example, causing its displaying).

An embodiment of the present invention can advantageously be employed for assessing/diagnosing any disease or pathology characterized by or related to changes in the macro and/or microcirculation of blood in an organ or tissue such as, for instance, those diseases or pathologies resulting in an increase or reduction of blood flow with respect to a normal physiological condition (such as ischemic, inflammatory and tumoral diseases or pathologies). An embodiment can further be applied to follow the natural development, stay or regression of a disease or of a pathological state in a selected organ or tissue, or the response of the disease to a therapeutic treatment thereof, by periodically (e.g., daily, weekly or monthly) assessing the changes in blood perfusion of said organ or tissue.

Examples of possible clinical applications where an embodiment of the present invention can advantageously be employed include the diagnosis and evaluation of ischemic and/or vascular diseases or pathologies determined, for instance, by regional variations of vascularization (e.g., associated with the presence of atherosclerotic plaques or thrombi) or by a general reduction of microcirculation (e.g., in case of chronic ischemic vasculopathy as a consequence of diabetes, hypertension, drug toxicity, or transplant rejection).

Typical examples of such diseases are coronary artery diseases (CAD), e.g., including myocardial infarction (MI) and angina pectoris, which are characterized by decreased flow of blood through the coronary arteries, usually caused by atherosclerosis. Depending on the extent of coronary artery stenoses, this may lead to reversible myocardial ischemia during rest and stress conditions or to myocardial infarction as acute manifestation of coronary artery occlusion, which may lead (if not treated appropriately) to myocardial necrosis. Timely detection and accurate diagnosis of CAD can thus lead to early and appropriate medical or interventional/surgical management of patients, limit future heart attacks, increase patient survival and reduce medical and social cost. The quantification of myocardial perfusion through the assessment of microcirculation functionality may help, for instance, to identify patients who should undergo coronary angiography or coronary artery imaging, to assess presence of significant stenosis for allocation to coronary intervention, to guide interventional and non interventional treatment strategies in ischemic (and non-ischemic) cardiac disease, to evaluate the progression of a myocardial ischemia, to confirm or rule out acute myocardial infarction (AMI) in patients with acute chest pain syndrome, to risk-stratify AMI patients undergoing thrombolysis or interventional treatment, to evaluate size and transmural extent of MI, to determine myocardial viability in post-MI and/or heart failure patients for prognosis and risk-stratification and for allocation to conservative or interventional treatment or to determine no-reflow after coronary intervention/thrombolysis in patients with acute MI, to assess myocardial perfusion in heart failure patients or patients with myocardial hypertrophy or patients with valvular heart disease. An embodiment of the present method can further be applied for following the evolution pattern and/or effectiveness of a therapeutic or surgical treatment of any of the above disease or pathologies, e.g., in case of pharmacological treatment or lysis of atherosclerotic plaques or thrombi or in the case of heart transplantation.

Other examples of ischemic conditions where embodiments of the present invention can advantageously be employed include the evaluation of cerebrovascular diseases or pathologies, including acute stroke. Cerebral ischemia is a decrease in cerebral blood flow with resultant decrease in cerebral oxygenation, most often caused by atherosclerotic disease of the extracranial carotid or cerebral arteries or by cardiac or vascular embolism. The method of an embodiment of the invention, applied to the quantification of microvascular anatomy/function or brain perfusion related parameters, may thus help to identify normal and abnormal brain perfusion and to better assess chronic or acute ischemic (i.e. stroke) cerebrovascular disease, for diagnosis, definition of area at risk, prognosis and monitoring during treatment, to assess cerebrovascular reserve in patients with extra- and/or intracranial vascular stenoses, to assess microvascular anatomy and function in patients with intracranial neoplasms or to assess cerebrovascular dysfunction in dementia/cognitive dysfunction syndromes and/or degenerative and/or inflammatory diseases of the brain.

Further examples of clinical applications involving ischemia, where an embodiment of the present invention can advantageously be employed, include the evaluation of ischemic kidney conditions, including renal artery stenosis. Renovascular diseases may occur in different forms, i.e. asymptomatic renal artery stenosis, renovascular hypertension, or ischemic nephropathy and treatment options include medical, surgical or percutaneous interventional approaches. The determination according to an embodiment of the present invention of parameters related to renal perfusion may help to identify normal and abnormal renal perfusion, allowing identification of the hemodynamic relevance of renal artery stenoses and the evaluation of medical and/or interventional treatment and provide prognostic information. The method can further be useful for evaluating liver-associated perfusion anomalies such as, for instance, the evaluation of the portal vein circulation and its capillary distribution in the liver (e.g., to assess degree of cirrhosis or drug toxicity), as well as perfusion anomalies in or associated to other organs, such as spleen, pancreas or gall bladder. An embodiment of the invention can also be used to assess the effectiveness of organ transplantations (for instance, kidney or liver) or tissue transplantation (for instance, skin grafts), such as by detecting undesirable ischemic conditions in the transplanted organ or tissue which could be related either to transplant rejection or drug toxicity.

An embodiment of the invention can further be used to assess possible variations in the arterial supply of the artery (vaso vasorum), which can be strongly altered when plaque formation occurs. As the vaso vasorum development can rapidly enhance upon cholesterol level increase in the arteries, the detection of vasa vasorum vessel (rapid) formation can thus indicate the possible presence of an atherosclerotic disease.

With regard to inflammatory diseases or pathologies, which are characterized by an increase of the perfusion in the inflamed areas, an embodiment of the present method can be useful for diagnosis, determination of extent, prognostic assessment and follow up during treatment.

Examples of inflammatory diseases are arthritis, in particular rheumatoid arthritis (RA), inflammatory bowel disease (IBD), inflammatory lymph-node diseases or post-trauma inflammations of tendons/muscles. Autoimmune diseases, such as the above-mentioned RA or IBD, are often associated with inflammatory processes.

Rheumatoid arthritis (RA) is a systemic inflammatory progressive disease of the joints, characterized by a chronic fluctuating course of remissions and exacerbations. During exacerbations pathologic joints are typically characterized by the presence of evident vasodilatation within the sinovia. Quantitative display of perfusion related parameters, according to an embodiment of the present invention, within the inflamed joint may be helpful to accurately diagnose and/or classify inflammatory arthritis/RA, to indicate the prognosis of patients with arthritis/RA, to monitor the efficacy of treatment of patients with arthritis/RA and decide when to stop the pharmacological treatment (the anti-inflammatory drug used to treat acute condition are often burdened by severe collateral effects and the improvement of symptomatology and laboratory markers are often not related to a complete remission of the disease).

IBD includes Crohn's disease (CD) and ulcerative colitis (UC). Both are idiopathic, life-long, destructive chronic inflammatory conditions of the gastrointestinal tract characterized by periods of exacerbation and remission. IBD affects quality of life due to symptoms (diarrhea, fistulas, fever, pain, associated surgical interventions, short bowel syndrome) and may have extraintestinal manifestations. Anti-inflammatory treatment consists of systemic or topic steroids, aminosalicylates, azathioprin, methotrexate and other drugs. The assessment of treatment response is often difficult and clinical scores (CDAI—Crohn's Disease Activity Index) are not always associated with concurrent reduction in laboratory markers for inflammation and/or histological remissions. Quantitative assessment of perfusion related parameters including quantification of microcirculation perfusion in the bowel wall may be helpful to accurately diagnose and/or classify IBD, to indicate the prognosis of patients with IBD and to monitor the efficacy of treatment of patients with IBD.

In post-trauma inflammations of tendons and/or muscles, a manifest change in the macrocirculation of muscles/tendons occurs. An embodiment of the present method can be helpful to precisely assess the extent of the injury and/or to monitor the efficacy of a therapeutic treatment of the inflammation.

With regard to applications in oncology, a method of an embodiment of the invention may be helpful to accurately diagnose (detect the presence) and/or classify (characterize) tumor disease (e.g., malignant vs. benign), to indicate the prognosis of patients with tumor disease, to monitor the efficacy of treatment with tumor disease or to facilitate identification of organ areas with malignant infiltration and allow directed diagnostic or therapeutic measures. The method can be used for all types of cancers as, for instance, breast cancer, malignant liver lesions, prostate cancer, pelvic tumours, lymph-node/lymphoma assessments, and so on. The quantification is able to differentiate the vascularization present in the tumor (neoangiogenesis), which is characterised by an organization different from the vascular organization of the normal tissues/organ. Example of detection of tumor is the identification of abnormal and disordered microcirculation within normal prostatic tissue.

Quantification methods are useful for assessing the treatment response of a tumor, such as in neoadjuvant tumor therapy in breast cancer. Locally advanced breast cancer (LABC) represents 5-20% of all newly diagnosed breast cancers and neoadjuvant chemotherapy has the objective to enable or improve operability of patients by reduction of the tumor-load. Another example is the response of liver metastasis to chemotherapy. The degree of response can guide duration of the treatment and possibly modifying it at an early time point, in order to optimize the results.

Ophthalmology and dermatology are other medical fields where the perfusion assessment method of an embodiment of the invention can be advantageously applied, for assessing possible pathologies associated with ischemic, inflammatory and/or tumoral conditions involving changes in the macro and/or microcirculation of blood.

Figure 8A:
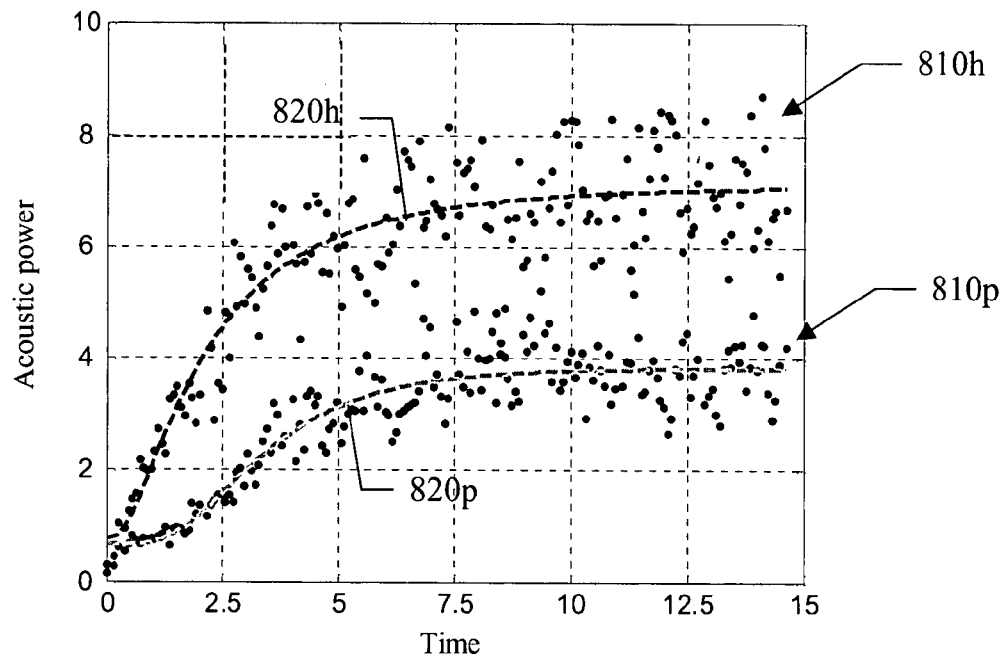
FIGS. 8a and 8b show the fitting of experimental data for healthy and pathological tissues, and the corresponding probability density distributions.
Figure 8B:
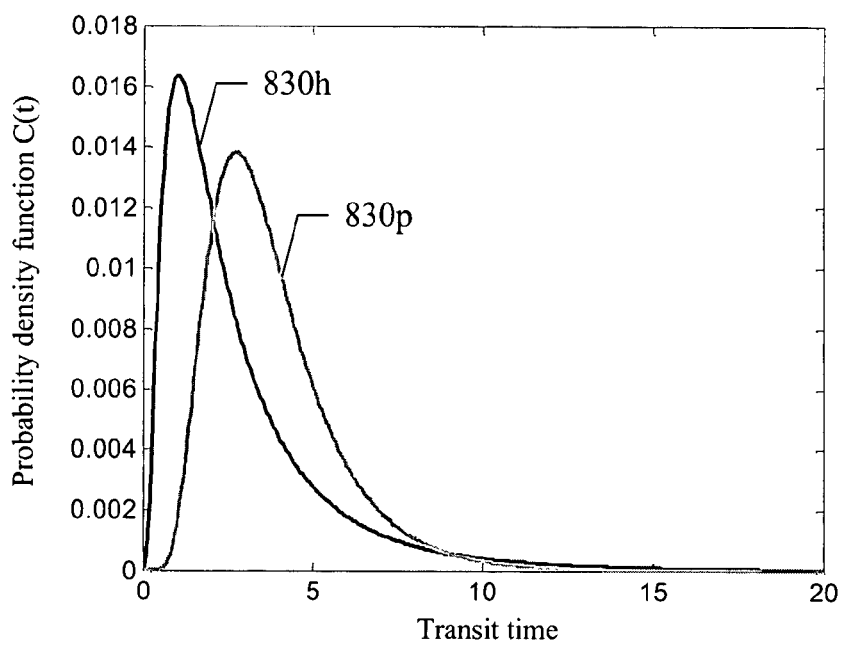

Experimental results relating to an application of a solution according to an embodiment of the invention are illustrated in FIGS. 8a-8b. Considering in particular FIG. 8a, the samples of the acoustic power measured over time for a body-part including healthy tissues and for a body-part including pathological tissues (in terms of Squared Root-Mean-Square, or $RMS^2$, values) are denoted with 810h and 810p, respectively. In both cases, the acoustic power was measured with a Sequoia ultrasound scanner (by Siemens) in a contrast-specific mode called Contrast Pulse Sequencing (CPS) with a convex array at a frequency of 3 MHz and a Mechanical Index of 0.25. The samples 810h relate to a ROI placed in the kidney cortex of a rabbit (representing healthy tissues), whereas the samples 810p relates to a ROI placed in a VX-2 tumor that was implanted on the rabbit kidney; the exposure conditions were similar for the two ROIs, since they were positioned at the same depth in the imaging plane and symmetric with respect to the main axis of the ultrasound probe. The samples 810h and 810p were fitted by corresponding perfusion functions E(t) using the predefined values K=1.33 $mm^{-1}$ and D=2.5 mm; particularly, a perfusion function 820h and a perfusion function 820p were obtained for the ROI in the kidney cortex and for the ROI in the VX-2 tumor, respectively.

As shown in FIG. 8b, the perfusion functions for the kidney cortex and for the VX-2 tumor are associated with corresponding probability density functions C(τ) 830h and 830p, respectively. The different organizations of the microvascular network in the kidney cortex and in the VX-2 tumour are clearly reflected by the shapes of their probability density functions 830h and 830p. Particularly, the probability density functions 830h for the kidney cortex is more asymmetric (y=4.04) than the one 830p for the VX-2 tumor (y=1.63).

Experimental results relating to a further application of a solution according to another embodiment of the invention are illustrated in FIGS. 9a-9b. Considering in particular FIG. 9a, a series of samples of the acoustic power measured for the same body-part at different times (in terms of $RMS^2$ values) are denoted with 905a, 905b, 905c and 905d. The samples 905a-905d relate to a ROI including a mammary adenocarcinoma tumor (MatBIII), starting at day 9 (905a) through day 10 (905b), day 11 (905c) and day 14 (905d) after its implantation. In all cases, the acoustic power was measured with a Sequoia ultrasound scanner (by Siemens) in a contrast-specific mode called Harmonic Imaging (HI) with a linear array at a frequency of 6 MHz and an MI of 0.26. The samples 905a-905d were fitted by corresponding perfusion functions 910a-910d using the predefined values K=1.33 $mm^{-1}$ and D=2.5 mm.

As shown in FIG. 9b, the perfusion functions for the different days are associated with corresponding probability density functions C(τ) 915a-915d. As can be seen, the evolution of the tumour is clearly reflected by the changing shape of the probability density functions 915a-915d. Particularly, the probability density functions 915a-915d become more and more asymmetric, with the corresponding skewness γ that takes the values 2.3 (day 9), 5.1 (day 10), 7.7 (day 11) and 9.0 (day 14); The progressive increase of the skewness γ indicates the strong change in the organization of the microvascular network of the tumour, which becomes more and more necrotic over the course of its growth.

MODIFICATIONS

Naturally, in order to satisfy local and specific requirements, a person skilled in the art may apply to the one or more solutions described above many modifications and alterations. Particularly, although the present invention has been described with a certain degree of particularity with reference to one or more embodiments thereof, it should be understood that various omissions, substitutions and changes in the form and details as well as other embodiments are possible; moreover, it is expressly intended that specific elements and/or method steps described in connection with any disclosed embodiment of the invention may be incorporated in any other embodiment as a general matter of design choice.

For example, similar considerations apply if the ultrasound scanner has a different structure or includes other units; likewise, the use of whatever contrast agent is contemplated. In addition, the principles of the invention also apply when different or additional perfusion parameters are taken into account.

In any case, the suggested formula for calculating the skewness γ are merely indicative; indeed, the use of any other indicator of the asymmetry of the probability density distribution is within the scope of the invention. Examples of alternative formulas for calculating the skewness include, but are not limited to the Pearson mode skewness:

$$\frac{[\text{mean}] - [\text{mode}]}{\sigma},$$

the Pearson's skewness coefficients:

$$\frac{3 \cdot [\text{mean}] - [\text{mode}]}{\sigma},$$

or $$\frac{3 \cdot [\text{mean}] - [\text{median}]}{\sigma},$$

or the Bowley skewness:

$$\frac{Q_1 - 2Q_2 + Q_3}{Q_3 - Q_1},$$

where the terms $Q_1$-$Q_3$ denote the interquartile ranges.

Moreover, the perf function may be defined in an equivalent manner.

Different techniques for linearizing the echo-power signal (to make it proportional to the concentration of the contrast agent in the body-part) are tenable. For example, when dealing with a raw echo-power signal proportional to the acoustic pressure, this result may be achieved simply by squaring the echo-signal amplitude.

Alternatively, the samples for the selected ROI may be obtained with equivalent algorithms. For example, in case the duration of the measured echo-power signal is insufficient to determine its final steady state, the value measured just before applying the destruction pulses may be used as the expected asymptotic value.

Similar considerations apply if other techniques are used for fitting the samples to the perfusion function (either in the continuous form or in the discrete form); for example, the initial vector of transit times τ[ ] may be selected in another way, or the probability vector C[ ] may be estimated directly (instead of the scaled probability vector $C_A$[ ]) by assuming the amplitude parameter A to be the asymptotic value of the sample vector E'[ ].

In any case, equivalent methods are suitable for minimizing the error function during the first estimation of the probability vector C[ ], for extrapolating the second estimate of the probability vector C[ ], or for training the neural network during the third estimation of the probability vector C[ ]. Moreover, the use of different numbers of transit times N (at each estimation) is contemplated.

Nothing prevents the use of alternative neural networks (for example, without any bias value). In any case, the weights (and the bias value) can be reset to other values or with a different periodicity.

Similar considerations apply if the skewness γ of the healthy tissues (to be compared with the one of the body-part under analysis) is obtained in another way.

Alternatively, different strategies can be implemented for monitoring the evolution of the skewness γ of the body-part over time.

In any case, an embodiment of the invention lends itself to be implemented with a program that is structured in a different way, or with additional modules or functions; likewise, the different memory structures can be of different types, or can be replaced with equivalent entities (not necessarily consisting of physical storage media). Moreover, an embodiment of the proposed solution can implement equivalent methods (for example, with similar or additional steps).

In any case, it is possible to distribute the program in any other computer readable medium (such as a DVD).

Moreover, it will be apparent to those skilled in the art that the additional features providing further advantages are not essential for carrying out the invention, and may be omitted or replaced with different features.

For example, the use of other shape indicators (in addition or in alternative to the skewness γ) is not excluded.

Even though in the preceding description reference has been made to the perf function, this is not to be intended in a limitative manner; indeed, an embodiment of the invention can be practiced with any other S-shape function. Examples of alternative S-shape functions include the hyperbolic tangent function, the sigmoid function, or any trigonometric or polynomial approximation thereof. For example, possible approximations of the perf function include:

$$\text{perf}(q) = \text{sigmoid}(2.406 \cdot q)$$

$$\text{perf}(q) = \tanh(1.203 \cdot q)$$

$$\text{perf}(q) = 0.5 \cdot [1 + \text{erf}(q)] \cong \text{sign}(q)\left(1 - \frac{1}{1 + a_1|q| + a_2 q^2 + a_3|q|^3 + a_4 q^4}\right)$$

where sign(q)=1 for q≧0 and sign(q)=−1 for q<0, and where $a_1$=0.278393, $a_2$=0.230389, $a_3$=0.000972, and $a_4$=0.078108.

Moreover, an embodiment of the proposed solution lends itself to be applied even on non-linearized echo-power signals (for example, images), which are not proportional to the concentration of the contrast agent in the body-part. In this case, the perfusion function is modified by the same process as the one causing the non-linearity (for example, square-root and log-compression).

Alternatively, an embodiment of the present invention can also be applied at the level of groups of visualizing elements (for example, determined according to the speckled nature of the images), or even at the pixel/voxel level.

In any case, the principles of the invention should not be limited to the (continuous or discrete) perfusion functions described-above; indeed, an embodiment of the solution of the invention is suitable to be applied more generally to any perfusion function based on whatever combination of (two or more) elementary perfusion functions with S-shape that are weighted according to the corresponding probability density distribution.

For example, the estimation of the probability density function C(τ) assuming a distribution other than the lognormal one is not excluded.

In different embodiments of the invention, the probability vector C[ ] may be estimated with other techniques. For example, it is possible to exploit a wavelet decomposition; in this case, a mother wavelet is preferably chosen as the second derivative of the perf function. Similar analysis may be based on the Fourier, Radon, Hilbert, Z- or any other integral transform.

It should be noted that the estimation of the probability vector C[ ] with a different number of steps (down to a single one) is within the scope of the invention.

Moreover, alternative training processes of the neural network, even without any periodic reset of the weighs, are feasible.

In any case, the principles of the invention should not be limited to the above-described applications. For example, it is possible to compare the measured skewness γ with predefined reference ranges for different healthy tissues. In addition, the calculated shape indicators can simply be provided to the operator (without any automatic comparison with other values).

The concepts of the present invention also apply to ultrasound scanners based on different detection schemes or using other measuring techniques.

Alternatively, the diagnostic imaging equipment consists of an ultrasound scanner and a distinct computer (or any equivalent data processing system); in this case, the measured data is transferred from the ultrasound scanner to the computer for its processing (for example, through the removable disk, a memory pen/key, or a network connection).

Similar considerations apply if the programs are preloaded onto the hard-disk, are sent to the system through a network, are broadcast, or more generally are provided in any other form directly loadable into the working memory of the system.

At the end, a method according to an embodiment of the present invention lends itself to be carried out with a hardware structure (for example, integrated in a chip of semiconductor material), or with a combination of software and hardware.

What is claimed is:

1. A perfusion assessment system including:
a device configured to:
provide an echo-power signal indicative of a reperfusion of a contrast agent in a body-part of a living subject following destruction of a significant portion of the contrast agent in the body-part; and
a processor configured to:
associate the echo-power signal to a perfusion function with an S-shape based on a plurality of elementary perfusion functions with said S-shape each one for a corresponding value of at least one perfusion parameter, the elementary perfusion functions being weighted according to a probability density distribution of the at least one perfusion parameter, wherein the S-shape comprises an initial portion with substantially zero first derivatives, a final portion with substantially zero first derivatives, and a central portion between the initial portion and the final portion changing monotonically from a value of the initial portion to a value of the final portion,
determine at least one shape indicator of the probability density distribution,
compare the at least one shape indicator with at least one predetermined further shape indicator to identify morphological characteristics of the body-part according to a result of the comparison.

2. The system according to claim 1, wherein the at least one shape indicator is indicative of a skewness of the probability density distribution.

3. The system according to claim 2, wherein each elementary perfusion function is a cumulative normal distribution function based on a first predetermined parameter indicative of an echo-power signal measure sensitivity and a second predetermined parameter indicative of a contrast agent destruction extent.

4. The system according to claim 2, wherein the processor is further configured to process the echo-power signal to be proportional to a concentration of the contrast agent in the body-part.

5. The system according to claim 2, wherein the associating comprises calculating a temporal sequence of samples representative of the echo-power signal in a region of interest, and fitting the samples by the perfusion function.

6. The system according to claim 1, wherein each elementary perfusion function is a cumulative normal distribution function based on a first predetermined parameter indicative of an echo-power signal measure sensitivity and a second predetermined parameter indicative of a contrast agent destruction extent.

7. The system according to claim 6, wherein the processor is further configured to process the echo-power signal to be proportional to a concentration of the contrast agent in the body-part.

8. The system according to claim 6, wherein the associating comprises for calculating a temporal sequence of samples representative of the echo-power signal in a region of interest, and fitting the samples by the perfusion function.

9. The system according to claim 1, wherein the processor is further configured to process the echo-power signal to be proportional to a concentration of the contrast agent in the body-part.

10. The system according to claim 1, wherein the associating comprises calculating a temporal sequence of samples representative of the echo-power signal in a region of interest, and fitting the samples by the perfusion function.

11. The system according to claim 1, wherein the probability density distribution is a lognormal function of the at least one perfusion parameter and the perfusion function comprises the integral of the elementary perfusion functions multiplied by the lognormal function, the perfusion function being represented by a set of fitting parameters, and wherein the determining the at least one shape indicator comprises calculating the at least one shape indicator from the fitting parameters.

12. The system according to claim 1, wherein the probability density distribution is represented by a vector of probabilities, the perfusion function including the summation of the elementary perfusion functions multiplied by the corresponding probabilities, and wherein the determining the at least one shape indicator comprises calculating the at least one shape indicator from the vector of probabilities.

13. The system according to claim 12, wherein the associating comprises determining a first estimate of the vector of probabilities by minimizing an error function between the echo-power signal and the perfusion function, the first estimate including a first number of elements, extrapolating a second estimate of the vector of probabilities from the first estimate, the second estimate including a second number of elements higher than the first number, and determining a third estimate of the vector of probabilities by a neural network being initialized according to the second estimate.

14. The system according to claim 13, wherein the neural network comprises a synapsis based on a plurality of weights corresponding to the vector of probabilities, the determining the third estimate including training the neural network by iteratively adjusting the weights according to the echo-power signal and corresponding evaluations of the elementary perfusion functions for a predefined set of values of the at least one parameter, and periodically resetting the weights.

15. The system according to claim 1, wherein the at least one further shape indicator relates to a further body-part of the living subject being in a healthy condition.

16. The system according to claim 1, wherein the at least one further shape indicator relates to the body-part at a time preceding the determination of the at least one shape indicator.

17. A diagnostic imaging equipment including ultrasound means for acquiring the echo-power signal and the perfusion assessment system according to claim 1.

18. A perfusion assessment method including the steps of:
providing an echo-power signal indicative of a reperfusion of a contrast agent in a body-part of a living subject following destruction of a significant portion of the contrast agent in the body-part,
associating the echo-power signal to a perfusion function with an S-shape based on a plurality of elementary perfusion functions with said S-shape each one for a corresponding value of at least one perfusion parameter, the elementary perfusion functions being weighted according to a probability density distribution of the at least one perfusion parameter, wherein the S-shape comprises an initial portion with substantially zero first derivatives, a final portion with substantially zero first derivatives, and a central portion between the initial portion and the final portion changing monotonically from a value of the initial portion to a value of the final portion,
determining at least one shape indicator of the probability density distribution, and
comparing the at least one shape indicator with at least one predetermined further shape indicator to identify morphological characteristics of the body-part according to a result of the comparison.

19. A non-transitory computer readable medium comprising instructions that when carried out by a computer processor, perform the steps of claim 18.

\* \* \* \* \*

UNITED STATES PATENT AND TRADEMARK OFFICE
CERTIFICATE OF CORRECTION

| | |
|---|---|
| PATENT NO. | : 8,021,303 B2 |
| APPLICATION NO. | : 11/823098 |
| DATED | : September 20, 2011 |
| INVENTOR(S) | : Peter Frinking, Marcel Arditi and Nicolas Rognin |

It is certified that error appears in the above-identified patent and that said Letters Patent is hereby corrected as shown below:

In Claims 3 to 5 of the patent, "The system according to claim 2" should read --The system according to claim 1--.

Signed and Sealed this
First Day of November, 2011

David J. Kappos
*Director of the United States Patent and Trademark Office*

UNITED STATES PATENT AND TRADEMARK OFFICE
CERTIFICATE OF CORRECTION

PATENT NO.      : 8,021,303 B2
APPLICATION NO. : 11/823098
DATED           : September 20, 2011
INVENTOR(S)     : Peter Frinking et al.

It is certified that error appears in the above-identified patent and that said Letters Patent is hereby corrected as shown below:

Column 23, line 65 (Claim 3, line 1) "The system according to claim 2" should read
--The system according to claim 1--.

Column 24, line 4 (Claim 4, line 1) "The system according to claim 2" should read
--The system according to claim 1--.

Column 24, line 8 (Claim 5, line 1) "The system according to claim 2" should read
--The system according to claim 1--.

This certificate supersedes the Certificate of Correction issued November 1, 2011.

Signed and Sealed this
Thirtieth Day of October, 2012

David J. Kappos
*Director of the United States Patent and Trademark Office*